US008295935B2

(12) United States Patent
Okun et al.

(10) Patent No.: US 8,295,935 B2
(45) Date of Patent: Oct. 23, 2012

(54) MULTIPLE LEAD METHOD FOR DEEP BRAIN STIMULATION

(75) Inventors: Michael S. Okun, Gainesville, FL (US); Kelly D. Foote, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 492 days.

(21) Appl. No.: 11/725,635

(22) Filed: Mar. 20, 2007

(65) Prior Publication Data

US 2008/0103547 A1 May 1, 2008

Related U.S. Application Data

(63) Continuation-in-part of application No. PCT/US2005/033730, filed on Sep. 20, 2005.

(60) Provisional application No. 60/611,660, filed on Sep. 21, 2004.

(51) Int. Cl.
*A61N 1/18* (2006.01)

(52) U.S. Cl. .......................................................... 607/45

(58) Field of Classification Search ..................... 607/45
See application file for complete search history.

(56) References Cited

U.S. PATENT DOCUMENTS

| 4,735,204 | A | 4/1988 | Sussman et al. |
| 5,342,409 | A | 8/1994 | Mullett |
| 5,716,377 | A | 2/1998 | Rise et al. |
| 6,306,403 | B1 * | 10/2001 | Donovan ............... 424/239.1 |
| 6,463,328 | B1 * | 10/2002 | John ............................ 607/45 |
| 6,620,415 | B2 * | 9/2003 | Donovan ............... 424/239.1 |
| 6,920,359 | B2 | 7/2005 | Meadows et al. |
| 6,950,707 | B2 * | 9/2005 | Whitehurst ..................... 607/58 |
| 7,349,743 | B2 * | 3/2008 | Tadlock ........................ 607/116 |
| 2004/0015205 | A1 | 1/2004 | Whitehurst et al. |

OTHER PUBLICATIONS

Katayama et al., "Deep Brain and Motor Cortex Stimulation for Post-Stroke Movement Disorders and Post-Stroke Pain.", Acta Neurochir Suppl., 2003; 87:121-3.*
International Search Report and the Written Opinion of the International Searching Authority, or the Declaration International Preliminary Report on Patentability.
Foote et al., "Ventrelis Intermedius Plus Ventralis Ores Anterior and Posterior Deep Brain Stimulation for Posttraumatic Holmes Tremor: Two Leads May Be Better Than One: Technical Note" *Neurosurgery* 56[ONS Suppl 2]:ONS-445, 2005.
Katayama et al., "Deep brain and motor cortex stimulation for post-stroke movement disorders and post-stroke pain." *Acta Neurochir Suppl.* 2003;87:121-3.
Linderoth et al., *Wall and Melzack's Textbook of Pain e-dition, 5th edition*, Chapter 37"Spinal cord and brain stimulation" Sep. 2005.

(Continued)

*Primary Examiner* — Carl H Layno
*Assistant Examiner* — Allen Porter, Jr.
(74) *Attorney, Agent, or Firm* — Edwards Wildman Palmer LLP; Peter F. Corless

(57) ABSTRACT

New methods for deep brain stimulation (DBS) surgery using two or more electrical leads are provided. The methods are useful for treating a wide variety of brain-associated disorders including movement-related disorders, psychiatric disorders, metabolic/eating disorders, memory disorders, and pain. Methods featuring stimulation of distinct target areas of a subject's brain, such as the thalamic ventralis intermedius (VIM) and the ventralis oralis (VOA/VOP) using multiple electrical leads for treatment of tremor provide superior clinical outcomes to stimulation with single leads implanted in these target areas.

9 Claims, 3 Drawing Sheets

OTHER PUBLICATIONS

MacMillian et al., "Involvement of Human Thalamic Neurons in Internally and Externally Generated Movements" *Journal of Neurophysiology* 91:1085-1090, 2004.

McClelland III et al., "Microelectrode recording-determined subthalamic nucleus length not predictive of stimulation-induced side effects" *Neurosurg Focus* 19 (5):E13, 2005.

Molnar et al., "Differences in neuronal firing rates in pallidal and cerebellar receiving areas of thalamus in patients with Parkinson's disease, essential tremor, and pain." *J Neurophysiol*. Jun. 2005;93(6):3094-101. Epub Feb. 9, 2005.

Montgomery "Deep brain stimulation for hyperkinetic disorders" 17 (1):E1, 2004.

Stewart et al., "Subthalamic Deep Brain Stimulator Therapy for the Treatment of Parkinson's Disease." Prebyterian Hospital of Dallas Neuroscience Center, Case No. 6 Jan. 2004, Figure 4A.

Tang et al., "Neuronal firing rates and patterns in the globus pallidus internus of patients with cervical dystonia differ from those with Parkinson's disease." *J Neurophysiol*. Aug. 2007;98(2):720-9. Epub May 30, 2007.

Katayama et al., "Subthalamic nucleus stimulation for Parkinson disease: benefits observed in levodopa-intolerant patients", *J Neurosurg* 95:213-221, 2001.

Yamamoto et al., "New method of deep brain stimulation therapy with two electrodes implanted in parallel and side by side", *J Neurosurg* 95:1075-1078, 2001.

Yamamoto et al., "Deep brain stimulation for the treatment of parkinsonian, essential, and poststroke tremor: a suitable stimulation method and changes in effective stimulation intensity", *J Neurosurg* 101:201-209, 2004.

Katayama et al., "Control of post-stroke involuntary and voluntary movement disorders with deep brain or epidural cortical stimulation." *Stereotact Funct Neurosurg* 69: 73-79, 1997.

\* cited by examiner

MULTIPLE LEAD METHOD FOR DEEP BRAIN STIMULATION

CROSS-REFERENCE TO RELATED APPLICATIONS

This application is a continuation-in-part of PCT application No. US2005/033730 entitled "Multiple Lead Method for Deep Brain Stimulation, filed Sep. 20, 2005, which claims priority to U.S. Provisional application No. 60/611,660, entitled "Multiple Lead Method for Deep Brain Stimulation," filed Sep. 21, 2004, which are hereby incorporated by reference in their entireties.

FIELD OF THE INVENTION

The invention generally relates to the medical fields of neurology and neurosurgery, and more particularly to methods for deep brain stimulation therapy for brain disorders.

BACKGROUND OF THE INVENTION

Many disorders of the human central nervous system are associated with abnormal patterns of physiologic activity in brain circuitry. One group of diseases involves abnormalities in a family of parallel circuits that control both motor and non-motor functions. These circuits belong to a group of structures known as the basal ganglia. It is recognized from research studies of animals and clinical studies in humans with brain injuries or diseases that rates and patterns of electrophysiological activity are abnormal in many basal ganglia circuits. Notable examples of human conditions involving these circuits include Parkinson's disease, various forms of tremor, and disorders involving muscle tone (dystonia). Other syndromes that do not involve movement also may have basal ganglia involvement (e.g. obsessive compulsive disorder, pain, etc.) Patients suffering from these conditions present with one or more of variety of symptoms of motor deficiency including tremor, muscle rididity, loss or impairment of voluntary muscle activity (akinesia or dyskinesia), and gait irregularity. They may also present with non-motor symptoms (depression, anxiety, OCD, etc.).

Debilitating movement disorders have been treated by non-reversible surgical ablation of affected brain circuits, for example by procedures such as thalamotomy or pallidotomy. Deep brain stimulation (DBS) therapy is an attractive alternative to such permanent surgeries, providing the distinct advantages of reversibility and adjustability of treatment over time. DBS is a treatment method that aims to change the rates and patterns of activity of brain cells by implanting a brain stimulator (i.e., an electrode, also known as a lead) into a target region in the brain known to be associated with movement, including the thalamus, subthalamic nucleus (STN), globus pallidus, internal capsule, and nucleus accumbens.

Electrical stimulation by DBS of a particular target region of the brain, in some cases bilaterally (i.e., using an electrode on each side of the brain to stimulate paired target regions located on each side of the brain) has been successfully used to treat symptoms of several movement disorders. For example, it has been reported in several studies that targeting of the STN is effective to alleviate symptoms of Parkinson's disease. Other areas of the brain that have been successfully targeted for this disease include the globus pallidus internus (GPi) and the ventro-lateral thalamus (VIM/VOP). Clinical results of DBS therapy for treatment of several movement disorders, including Parkinson's disease and essential tremor, have been recently reviewed in Tronnier et al., Minim. Invas. Neurosurg. 45:91-96, 2002 and in Pollack et al., Movement Disorders 17:575-583, 2002).

Despite documented successes of DBS for some forms of Parkinson's disease and essential tremor (Benabid, A. L., et al., Stereotact Funct Neurosurg, 1994. 62(1-4):76-84; Benabid, A. L., et al., J Neurol, 2001. 248 Supply. 3: III37-47), many movement disorders are unresponsive or only partially benefited by current DBS procedures. Additionally, the success of DBS procedures can diminish over time. Thalamic lesioning (Kim, M. C., et al., J Neurol Neurosurg Psychiatry, 2002. 73(4):453-5; Deuschl, G., et al., Ann Neurol, 1999. 46(1):126-8; Krauss, J. K., et al., J Neurosurg, 1994. 80(5): 810-9) and thalamic DBS (Pahwa, R., et al., Mov Disord, 2002. 17(2):404-7; Samadani, U., et al., J Neurosurg, 2003. 98(4): 888-90) have both failed to consistently alleviate tremors due to structural and post-traumatic lesions affecting the cerebellothalamic and dopaminergic systems. Surgical treatment of a similar tremor associated with multiple sclerosis has also been relatively ineffective (Berk, C., et al., J Neurosurg, 2002. 97(4):815-20; Hooper, J., et al., Br J Neurosurg, 2002. 16(2):102-9; Schulder, M., et al., Stereotact Funct Neurosurg, 1999. 72(2-4): p. 196-201). Thus, there is an ongoing need for improved therapy for these conditions.

In recent years there has been a growing appreciation that DBS methods are applicable to a much wider range of brain-associated disorders than previously appreciated. Accordingly, there is a need for improved DBS therapies for treating a variety of conditions involving abnormal physiology of the brain.

SUMMARY OF THE INVENTION

The present invention provides a new method for deep brain stimulation for treatment of brain disorders. More specifically, the invention features the use of multiple electrical leads to eliminate or alleviate symptoms of a variety of disorders, including movement-related disorders, psychiatric disorders, metabolic/eating disorders, memory disorders, and disorders involving pain.

In particular, we have found that placement of multiple leads in appropriate positions in the brain of patients, and stimulation of one or more of these leads, can result in dramatic improvement in control of symptoms of the disorders, including improved therapeutic results as compared with those obtained using a single lead.

Accordingly, and in one aspect, the invention provides a method of deep brain stimulation (DBS) for treatment of a disorder associated with the brain. The method comprises positioning two or more electrical leads remote with respect to each other in the brain of a subject having a need thereof. Following placement of the leads in the brain of the subject, the method includes applying electrical stimulation to at least one of the electrical leads. Application of the electrical stimulation eliminates or ameliorates at least one symptom of the brain disorder.

Brain-associated disorders that can be effectively treated by the method are not particularly limited and can include, e.g., movement-related disorders, psychiatric disorders, metabolic/eating disorders, memory disorders, and pain.

Movement-related disorders suitable for treatment with the method can include Parkinson's disease, Huntington's disease, Tourette/OCD, tremor, epilepsy, and dystonia. The movement-related disorders can include tremors of various origins including complex tremor, parkinsonian tremor, dystonic tremor, monoclonic tremor, essential tremor, poststroke tremor, post-traumatic tremor, Huntington's disease, chorea, Tourette/OCD, multiple sclerosis tremor, and dystonia. Symptoms of movement-related disorders that can be eliminated or ameliorated by the method also are not limited and may include, inter alia, tremor, rigidity, akinesia, tic, akathesia, restlessness, and gait irregularity.

Psychiatric disorders or symptoms that can be treated by the method can include depression, mania, phobia, OCD, schizophrenia and addiction.

Metabolic/eating disorders that can be treated by the method include obesity, anorexia nervosa, vomiting disorders and bulimia nervosa.

In one version of the method, the electrical leads can be positioned within two or more anatomically or physiologically distinct target regions within the brain.

Depending upon the condition to be treated, the anatomically or physiologically distinct target regions of the brain will vary, and can include regions of the brain such as area 25, anterior limb of internal capsule, nucleus accumbens, inferior peduncle, paramedian nucleus, subthalamic nucleus, globus pallidus, hypothalamus, thalamus, subthalamus, centromedian nucleus of thalamus, ventral intermediate nucleus of thalamus (VIM), nucleus ventralis oralis (VOA), posterior region of the nucleus ventralis oralis (VOP), pallidal receiving area (VOA/VOP), insula, medial leminiscus, brainstem nuclei, cerebral cortex, temporal lobe, and medial forebrain bundle.

One preferred method in accordance with the invention is directed to treatment of a movement-related disorder. In this method, the selected anatomically or physiologically distinct target regions can include, e.g., the cerebellar receiving area (thalamic ventral intermediate nucleus, VIM), the anterior region of the nucleus ventralis oralis (VOA), the posterior region of the nucleus ventralis oralis (VOP) and the pallidal receiving area (VOA/VOP).

In a preferred embodiment of this method useful, e.g., for treatment of post-traumatic tremor, at least one of the electrical leads is positioned within the cerebellar receiving area (VIM) and at least one other electrical lead is positioned in the pallidal receiving area (VOA/VOP).

Another preferred embodiment of the method is directed to treatment of a psychiatric disorder. In this application, the selected anatomically or physiologically distinct target regions of the brain can include, e.g., one or more of area 25, anterior limb of internal capsule, nucleus accumbens, inferior peduncle, thalamus, hypothalamus, subthalamus and cortex.

Another preferred embodiment of the method useful for treating obesity can target two or more sites within the hypothalamus.

In a method of treatment for pain in accordance with the invention, the target regions of the brain are selected from insula, centromedian thalamus or other areas of thalamus, medial lemniscus and cortex.

For treatment of memory disorders, two or more electrical leads can be positioned in brain areas selected from thalamus, subthalamus, medial forebrain bundle, cortex, and temporal lobe.

Electrical current suitably can be applied in several ways to the electrical leads. In one variation, the current can be applied intermittently, to at least one of the electrical leads. Electrical current can also be applied continuously, to at least one of the electrical leads. The electrical current can be applied alternately to electrical leads in different target regions of the subject's brain, or it can be applied concurrently to electrical leads in several target regions of the subject's brain.

Other aspects of the invention are discussed below. The invention may be better understood by reference to one or more of the following drawings in combination with the detailed description of specific embodiments presented herein.

Unless otherwise defined, all technical terms used herein have the same meaning as commonly understood by one of ordinary skill in the art to which this invention belongs. Whereas methods and materials similar or equivalent to those described herein can be used in the practice or testing of the present invention, suitable methods and materials are described below. The particular embodiments discussed below are illustrative only and not intended to be limiting.

BRIEF DESCRIPTION OF THE DRAWINGS

The drawings form part of the present specification and are included to further demonstrate certain aspects of the present invention.

DETAILED DESCRIPTION OF THE INVENTION

Figure 1:
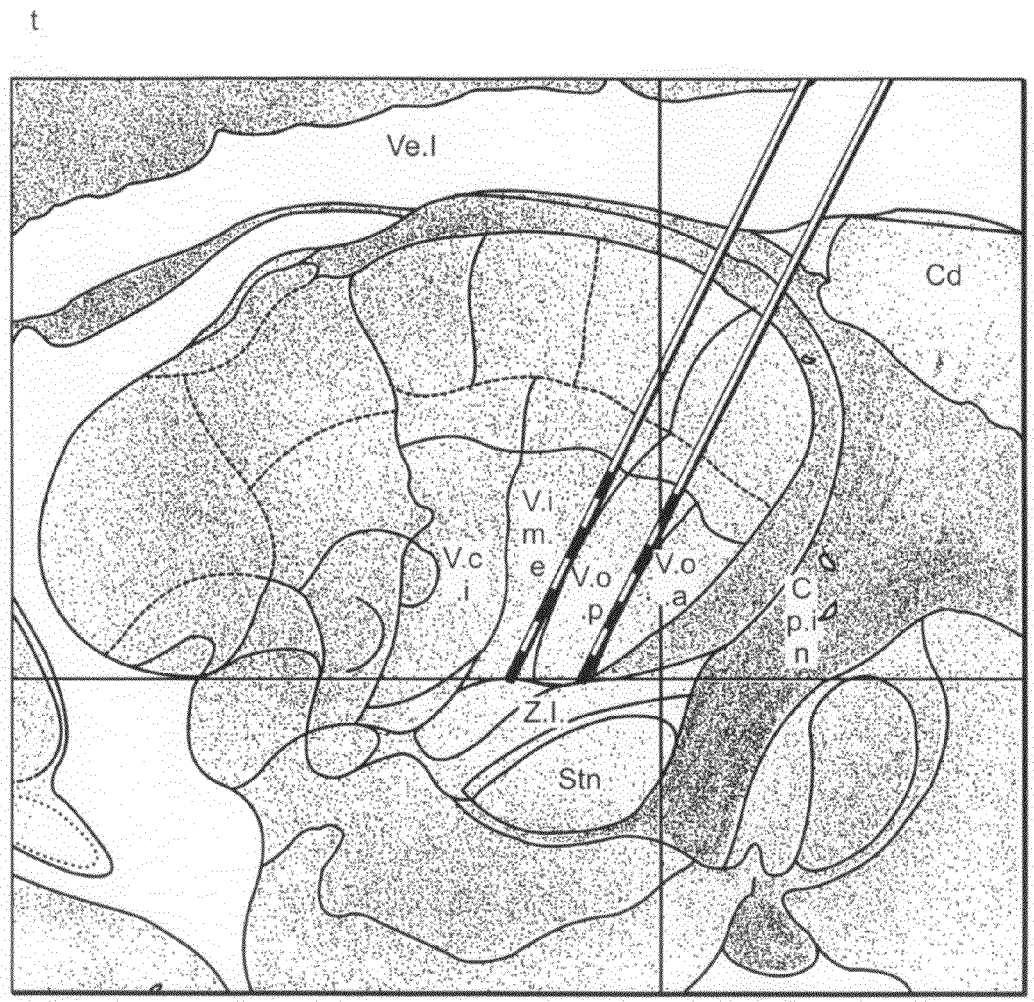
FIG. 1 is a drawing showing placement of two leads (10, 20) implanted in the brain of a patient with post-traumatic tremor, according to an embodiment of the invention.

The methods of the invention relate to improved procedures and clinical outcomes using deep brain stimulation (DBS) to stimulate selected groups of cells of the brain in subjects with disorders associated with the brain. As used herein, the term "disorder associated with the brain" and "brain disorder" is meant to encompass all disorders (or symptoms thereof) that originate in the brain or other parts of the body, which can be affected by electrical stimulation of cells or target regions within the brain. There is recognition of an ever-growing list of disorders and conditions that are governed or modulated at least in part by the activity of neurons in the brain. For example, studies have associated particular areas of the brain with a variety of conditions including movement-related disorders; disorders with a psychiatric component such as depression, obsessive compulsive disorder (OCD), manias, phobias, eating and vomiting disorders and the like ("psychiatric disorders"); obesity; memory disorders; and disorders involving pain such as headache. It is likely that this list will continue to grow as knowledge of the functions associated with particular target regions of the brain continues to expand. Accordingly, a large number of conditions and disorders are intended to be encompassed by the term "disorder associated with the brain."

DBS is an advanced neurosurgical procedure typically performed by a clinical team including neurologists, neurosurgeons, neurophysiologists and other specialists trained in the assessment, treatment and care of neurological conditions. Briefly, following selection of an appropriate patient and determination of the brain region to be targeted (using methods described below), precise placement of an electrode or lead in the patient's brain is carried out in an operating room setting, typically utilizing advanced brain imaging technology and stereotactic targeting. After administration of local anesthesia, the patient undergoing electrode implantation experiences little discomfort, and is generally kept awake during the implantation procedure to allow communication with the surgical team.

Post-operative control of the electrical stimulation is by means of a stimulator unit or pulse generator similar to a pacemaker that is generally implanted subcutaneously, typically in the pectoral region of the patient. Following recovery from the implantation surgery and connection of the lead to the stimulator unit, the patient is monitored on an out-patient basis by specialists who perform tests to establish optimal settings for the electrical stimulation based on the patient's particular motor disability and response to stimulation, and teach the patient how to use the device.

Previous applications of DBS to treat movement disorders such as Parkinson's disease, essential tremor and other conditions have utilized either a single electrical lead implanted in a patient's brain, or a pair of leads implanted bilaterally to provide electrical stimulation to a single target region of the brain, such as the subthalamic nucleus (STN), which occurs as a pair of nuclei located on the left and right sides of the brain. As described above, stimulation with a single DBS lead has been shown to be sufficient and very effective to control symptoms of certain movement disorders, such as some types of Parkinson's disease and essential tremor, and has been approved by the FDA for treatment of these two conditions.

In contrast to previous studies, the inventors have made the unexpected discovery that whereas stimulation of the brain with one DBS lead can be insufficient, the implantation and stimulation of multiple electrical leads can provide a striking improvement patient outcome, for example in the motor control of patients with movement disorders such as post-traumatic tremor (Holmes tremor), and in tremor associated with multiple sclerosis.

Based on this discovery, the invention provides in one aspect a method of deep brain stimulation for treatment of a brain-associated disorder that includes positioning two or more electrical leads remote with respect to one another in the brain of a subject suffering from a brain-associated disorder.

Regarding the placement of the electrodes in the brain of the subject, the terms "remote with respect to one another" or "remote from one another," as used herein, can refer to remoteness in three-dimensional space (i.e., the distance between the electrodes), with the exception that two leads, each placed into the same functional area on opposite sides of the brain, such as the left and right subthalamic nuclei (STN), are not considered to be remote from one another. Similarly, two or more leads positioned within a single target region of the brain are not considered to be remote from one another if the distance between the electrodes is so small as to permit passage of electrical current from one electrode to another. However, in some applications two or more electrodes can be effectively positioned remote to one another within a single target area of the brain, such as in the hypothalamus, e.g., in the treatment of obesity.

Two or more leads can also be remote from one another if the electrical stimulation from the two or more electrodes affects two or more anatomically or physiologically distinct regions of the brain. As used herein with respect to identifiable regions of the brain, the term "anatomically or physiologically distinct" refers to target regions of the brain that may be distinguished and localized to specific positions in three-dimensional space by suitable techniques well known to those of skill in the art. Typically, such regions are comprised of cells or fibers with a different recognized functional or physiological activity, which may be detected, for example, by microelectrode recording.

The anatomical distribution, spatial mapping coordinates within the skull, and functional significance of distinct groups of human brain cells have been extensively studied and are the subject of numerous medical treatises in the field of functional neuroanatomy and neurosurgery. See, for example, Buren et al., Variations and Connections of the Human Thalamus, Springer-Verlag, New York (1972), or well known stereotaxic atlases such as Schalebrandt and Baily, and Schalebrandt and Wharren.

The methods of the invention can be used to target two or more distinct regions of the brain in the treatment of diverse brain-associated disorders. Table 1 provides a listing of brain disorders and presently known target regions of the brain for which it is believed that treatment with the multiple lead method of the invention can be effective.

TABLE 1

Brain-Associated Disorders and Suitable Target Sites for Placement of Multiple DBS Leads

| Brain Disorder | Target Sites† |
|---|---|
| Parkinson Disease | paramedian nucleus and brainstem nuclei |
|  | subthalamic nucleus |
|  | globus pallidus |
|  | cortex |
|  | thalamus |
| Obsessive Compulsive Disorder | area 25 |
|  | anterior limb of internal capsule |
|  | nucleus accumbens |
|  | inferior peduncle |
|  | cortex |
| Tourette Syndrome | centromedian nucleus thalamus |
|  | globus pallidus |
|  | anterior limb internal capsule |
|  | nucleus accumbens |
|  | thalamus |
| Tremor | thalamic ventral intermediate nucleus (VIM) |
|  | anterior region of nucleus ventralis oralis (VOA) |
|  | posterior region of nucleus ventralis oralis (VOP) |
|  | pallidal receiving area (VOA/VOP). |
|  | other thalamic regions |
| Epilepsy | anterior nucleus of the thalamus |
|  | centromedian thalamus |
|  | other specific areas (depending on the electroencephalogram) |
| Pain | insula |
|  | centromedian thalamus |
|  | other areas of thalamus |
|  | medial lemniscus |
|  | cortex |
| Cluster Headache | hypothalamus |
|  | thalamus |
|  | subthalamus |
| Depression | area 25 |
|  | anterior limb of internal capsule |
|  | nucleus accumbens |
|  | inferior peduncle |
| Obesity | hypothalamus |
| Eating Disorders | thalamus, hypothalamus |
|  | subthalamus |
|  | cortex |
| Dystonia | paramedian nucleus and brainstem nuclei |
|  | subthalamic nucleus |
|  | globus pallidus |
|  | cortex |
|  | thalamus |
| Memory disorders | cortex |
|  | thalamus |
|  | medial forebrain bundle |
|  | temporal lobe |
|  | subthalamus |

†Multiple leads may be positioned in one or a combination of the indicated target sites in the brain.

The method of the invention can utilize any electrode or electrical lead suitable for DBS therapy. As used herein, the terms "electrode" and "electrical lead" are interchangeable and used in their broadest sense to encompass a stimulation lead, a sensing lead or a combination thereof, or any other elongated member such as a catheter which may be usefully passed to a target within the brain and used for electrical stimulation of brain cells.

Generally, stimulation of a target region in a subject's brain involves contacting the region with an electrode capable of delivering an electrical signal to the region. A variety of electrodes can be employed for delivering the stimulation. For example, suitable electrodes include the deep brain stimulation electrodes used in Katayama, "Characterization and Modification of Brain Activity with Deep Brain Stimulation in Patients in a Persistent Vegetative State: Pain-Related Late Positive Component of Cerebral Evoked Potential," Pace, 14:16-121 (1991), and the Medtronic™ DBS 3280 (available from Medtronic, Minneapolis, Minn.), which has flexible TEFLON-SILASTIC™ coated, platinum iridium electrodes with four contacts, 4 mm tips, 2 mm mean tip separation, and an impedance of 5-7 kΩ within the brain, described, for example, in Velasco et al., Electroencephalography and Clinical Neurophysiology, 102:461-471 (1997).

Preferably the electrode is an implantable multipolar electrode designed for use with an implantable pulse generator that can be a radiofrequency controlled device operated by an external transmitter. Preferably, the multipolar electrode contacts should allow for adjustment of frequency (or "rate"), amplitude, and pulse width within at least the following respective ranges: about 2-200 Hz, about 0.1-10 Volts, and about 50-500 microseconds. More preferably, the multipolar electrode contacts allow for adjustment in a broader range than those recited above, particularly toward higher intensities. Such preferred electrodes include a Medtronic™ 3387 electrode (available from Medtronic, Minneapolis, Minn.) and are described, for example, in Benabid et al., J. Neurosurgery, 84:203-214 (1996). Another suitable lead is a deep brain stimulation electrode combined with a microelectrode recording probe, for example as described in U.S. Pat. No. 6,301,492 to Zonenshayn (2001) and in U.S. Pat. No. 6,343,226 to Sunde et al. (2002).

The multiple electrodes used in accordance with the invention can be positioned in the brain by methods conventionally used for positioning of single electrodes for deep brain stimulation. As is known in the art, the particular procedures used by teams of specialists skilled in DBS neurosurgery will vary according to the available equipment, training of personnel and the circumstances of each case. Details of the surgical procedures employed by several groups are described, for example, in Benabid et al., Movement Disorders 17 (Suppl. 3): S123-129 (2002) and in Schrader et al., Movement Disorders 17 (Suppl. 3): S167-174 (2002). Generally, the procedures for placement and testing of the single electrodes are divided into several steps including mounting of a stereotactic ring (also known as a CRW head ring) on the patient's skull under general anesthesia, and imaging by high resolution stereotactic commuted tomographic (CT) scanning of the head. The stereotactic CT scan is preferably preceded by high resolution, volumetric, three telsa magnetic resonance imaging (MRI) in advance of placement of the stereotactic head ring.

Planning of the surgical target sites within the brain and trajectories for approach to the selected targets is achieved using high quality MR images and computer software designed for stereotactic targeting such as Stereoplan Plus 2.3 (Stryker-Leibinger, Friedburg, Germany), SNS 3.14 (Surgical Navigation Specialists, Mississauga, Canada), or software as described in an Example below which facilitates navigation in "atlas space" using a three-dimensional orthogonal Cartesian coordinate system centered on the patient's mid-commissural point, which is readily defined by identifying the anterior and posterior commissures (AC, PC, respectively) and a non-colinear midpoint line in the patient's brain. Using these points as references, the target and trajectory are selected in atlas space and the corresponding coordinates on the stereotactic CRW head ring are automatically generated and used to set the CRW ring.

Following selection of the target region and computer-assisted planning of the surgical approach as described, the electrode is positioned in the brain of the subject through a burrhole that is made at a suitable location in the subject's skull. The placement of the electrode within a millimeter or less of the optimal target is generally required to improve symptoms and to avoid side effects. To improve accuracy of the final electrode placement, placement of the electrode is preferably tested during the implantation procedure, for example by microelectrode recording to measure characteristic electrical patterns produced by cells in the target region. Methods for microelectrode recording for DBS electrode placement are described, for example, in Schrader et al., supra, and in Examples below.

The effectiveness of the electrode placement can be assessed intraoperatively by applying current to the electrode (macrostimulation) and measuring its ability to alleviate a symptom, such as a tremor. With the patient awake and locally anesthetized, stimulation is performed to define the borders of the target structures and to evaluate effects and side effects. The microelectrode placement that shows the best results is used to determine the position of the permanent electrode, which is placed under fluoroscopic X-ray control. The electrode is fixed at the rim of the burrhole, for example with a titanium miniplate. External macrostimulation with a screening device such as a Model 3625 (Medtronic, Minneapolis, Minn.) is preferably performed immediately after fixation of the electrode, to reproduce the stimulation effects observed intraoperatively with the microelectrode, and to rule out unwanted side effects. Correct positioning of the electrode is subsequently documented by skull X-ray.

After placement, the electrode remains implanted and in a subsequent operation the patient under general anesthesia is subcutaneously implanted with a stimulator unit, such as an Intrell™ II (Medtronic, Minneapolis, Minn.), which is connected to the electrode to permit application of electrical current to the electrode.

In the routine practice of DBS methods, initiation and optimization of the electrical stimulation therapy is achieved in a series of DBS programming sessions in which adjustments are made to deep brain stimulator settings (such as pulse width, frequency, and amplitude) by a specialist trained in movement disorders, according to the individual patient's condition, the site of electrode placement within the brain, and the patient's response upon testing. Methods for programming of DBS stimulators are known in the art and have been described, for example, in Volkmann et al., Movement Disorders 17 (Suppl. 3):S181-187, and in Dowsey-Limousin, Movement Disorders 17 (Suppl. 3): S208-211.

Multiple Lead Method for Treating Movement Disorders

One preferred aspect of the invention is a method of treatment for a movement-related disorder. The term "movement disorder," or "movement-related disorder," as used herein, is defined broadly to include any disease or condition that abnormally affects the motor nerves or muscles of the body, in particular those that abnormally affect movement, resulting in either excessive movement (hyperkinesias) or insufficient movement (bradykinesia). Diseases and conditions considered to be, or to involve, movement disorders include, for example, ataxia, blepharospasm, chorea, dysphonia, dystonic disorders, gait disorders, Huntington's disease, multiple sclerosis, myoclonus, Parkinson's disease, spasticity, tardive dyskinesia, tics, Tourette syndrome/OCD, and various forms of tremor, including but not limited to complex tremor, rest, postural or action tremor, parkinsonian tremor, dystonic tremor, myoclonic tremor, essential tremor, poststroke tremor, multiple sclerosis tremor, and post-traumatic (Holmes) tremor.

A non-limiting example of an effective treatment for a movement-related disorder in accordance with the invention includes placing remotely positioned leads in anatomically or physiologically distinct regions of the brain, wherein at least one lead is positioned to stimulate a cerebellar receiving area of the brain such as the VIM, and at least one lead is positioned to stimulate a pallidal receiving area such as the VOA/VOP. As further described in Examples below, this method can be highly effective for treatment of tremor. A young man with a 16-year history of Holmes tremor so debilitating as to prevent him from going to school or working was implanted with two DBS electrodes. As shown in FIG. 1, one electrode 10 was positioned in the thalamic VIM nucleus (thought to be a cerebellar receiving area) and another electrode 20 was positioned remotely from the first, i.e., in the thalamic VOA/VOP region (thought to be a pallidal receiving area).

Figure 2:
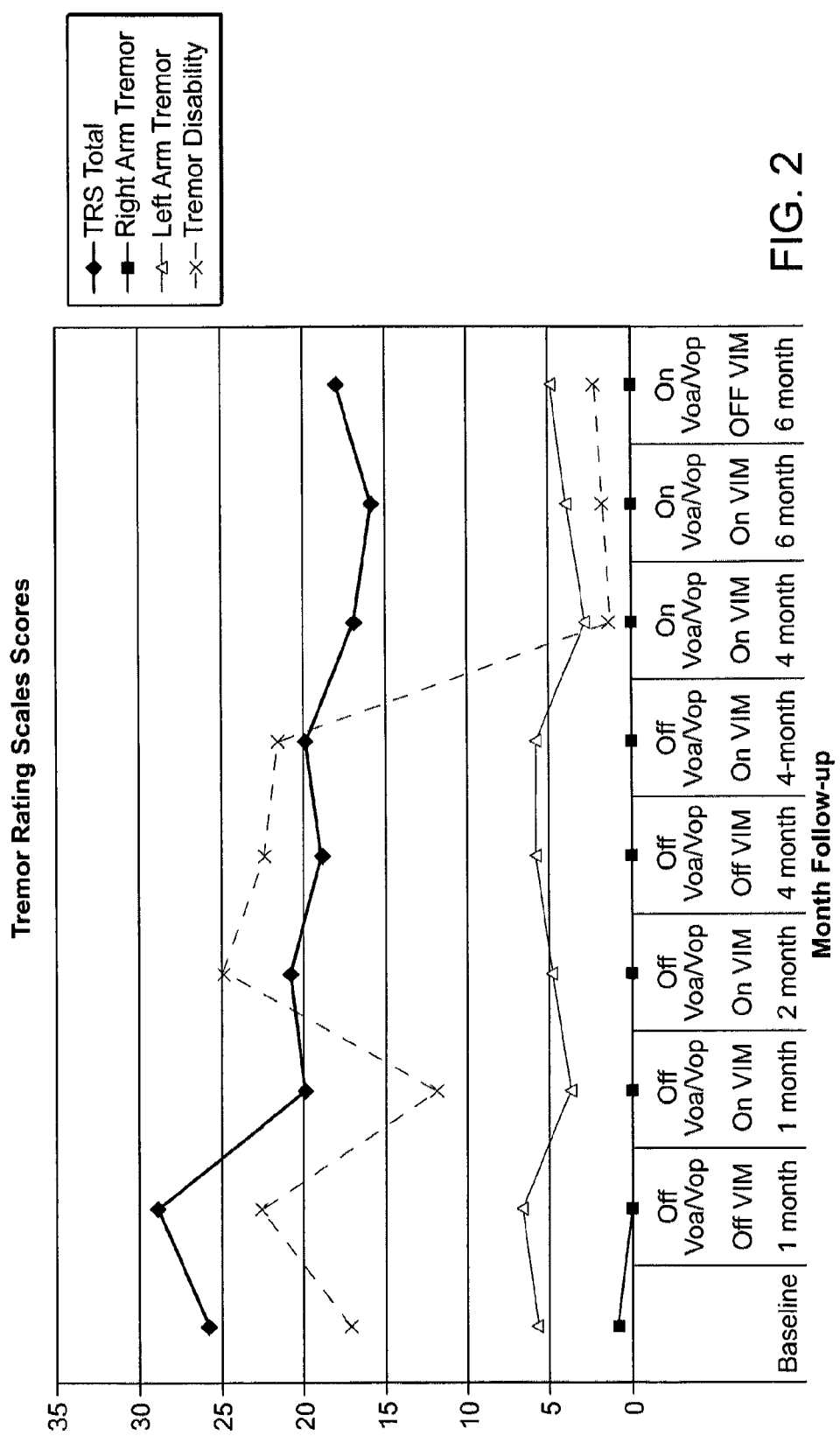
FIG. 2 is a graph showing outcomes of stimulation with DBS leads as measured by standardized tremor rating and tremor disability rating scales.

Stimulation with the VIM electrode alone resulted in reduction of the patient's tremor, but not enough to significantly alter his disability score. As shown in FIG. 2, tremor benefit with VIM stimulation alone declined over time, with tremor rebound manifesting after one to two months on VIM stimulation. After two months of VIM stimulation with the VOA/VOP electrode turned off, the VOA/VOP stimulator was then activated, at which time the patient experienced a marked and sustained improvement in tremor and disability, up to the end of the follow-up period (FIG. 2). The patient was able to obtain gainful employment. As further described below, successful outcomes were also reached in two other patients with post-traumatic tremor and one patient with tremor associated with multiple sclerosis.

The method of treatment for a movement-related disorder can be highly effective for treatment of tremor. In variations of methods in accordance with the invention, effective therapy can be achieved, depending upon the subject's response, by varying the DBS stimulation protocol to optimize the results. For example, the electrical stimulation can include a period in which electrical current is applied alternately to at least two electrical leads implanted in the subject's brain. As a non-limiting example, in subjects having two leads implanted in the VIM and VOA/VOP target regions, stimulation can be applied to the alternate leads under conditions of VIM On, VOA/VOP Off, or VIM Off, VOA/VOP On. Stimulation can also be applied wherein electrical current is applied concurrently to both electrical leads (for example, VIM On, VOA/VOP On). Combinations of the alternate and concurrent stimulation protocols are also possible, for example, a period of stimulation with VIM On, VOA/VOP Off, or VIM Off, VOA/VOP On, followed by a period of stimulation with both VIM and VOA/VOP On. Electrical current can be applied either intermittently or continuously.

Standardized test methods (for example, tremor and disability rating scales) for assessment of myriad symptoms of motor disabilities are known to those of skill in the art, and can be used to determine the optimal conditions for electrical stimulation, to eliminate or ameliorate a particular symptom. Additionally, the tests of motor function can be advantageously combined with various tests of the neuropyschological status of the subject, as further described in an Example below.

It is believed that the multiple lead DBS method described herein has potential application for a wide range of movement disorders. In general, candidates for this therapy meet the clinical criteria proposed or used for single-lead DBS. Selection criteria for patients with several forms of movement disorders who are good candidates for DBS therapy are described, for example, in Okun and Vitek, supra, and in Okun et al. Neurology 63:161-163 (2004).

The inventive method is thought to be particularly useful for treatment of those movement disorders that are refractory to treatment with medication (such as medication typically prescribed for Parkinson's disease, e.g., levodopa). Medical therapy useful in the treatment of Parkinson's disease and other movement disorders is described, for example, in Okun et al., in Parkinson's Disease: Pathophysiology and Medical Therapy Textbook Chapter: Neurosurgery (Maciunas, ed.). Medical therapy used in the treatment of dystonia is described, for example, in Okun and Vitek, Surgery for Dystonia, in Yeoman's Textbook of Neurosurgery (Bakay, ed.).

Other patients who might benefit from the method of the invention are those whose movement-related disorder is known or suspected to result from a pathophysiological mechanism involving more than one anatomically distinct region of the brain, or one which originates in a region of the brain such as the thalamus in which the affected area is too large to be stimulated by a single electrode.

Selection of the particular target region(s) of the brain for placement of the multiple electrodes is guided by diagnostic assessment of an individual patient's symptoms and knowledge of, or insight into (for example from results of research studies) the underlying pathophysiological mechanism of the condition. Patho-physiological mechanisms involved in various movement disorders continue to be discovered and are described in recent references, including, for example, Yelnik, Movement Disorders 17 (Suppl. 3):S15-S21; Nandi et al., Movement Disorders 17 (Suppl. 3):S15-S21; Bergman and Deutsch, Movement Disorders 17 (Suppl. 3):S28-S40; Deutsch and Bergman, Movement Disorders 17 (Suppl. 3):S41-48; and Theodosopoulos et al., Movement Disorders 18:791-798.

EXAMPLES

The present invention is further illustrated by the following specific Examples, which should not be construed as limiting the scope or content of the invention in any way.

Example 1

Clinical Case Study: Holmes Tremor

A 24-year-old, African-American man with a 16-year history of debilitating left upper extremity tremor presented for evaluation and treatment. At age eight, he sustained a closed head injury when he was struck by a car while crossing a street on foot. A left hand tremor developed a few months after the accident, and remained severe and unchanged 8 years. During his subsequent evaluation he was noted to have left-sided rest, postural and action tremor. He complained that his intentional tremor prevented him from holding a job, and that the tremor resulted in his discontinuation of schooling. He was treated with low dose Olanzepine (5-10 mg) several years after his accident for explosive behavior. He reports that since treatment he no longer has a problem with anger outbursts. He tried high dose dopamine (carbidopa/levodopa 1 gram) for his tremor without improvement. His general physical examination and vital signs were normal. His neurological examination revealed an intact mental status. He had mild dysfluency, which, according to the patient and past chart records, had been present and stable since the accident. His language examination was otherwise normal. His cranial nerves, sensory, motor, cerebellar, and deep tendon reflexes were all normal. He walked with a very slight hemiparetic gait, with mild circumduction of the left leg. He had a left sided Holmes tremor (mild 2-3 Hz left-sided resting tremor, moderate postural tremor, and severe intentional tremor). Head MRI was normal.

Example 2

Methods for DBS Target and Trajectory Selection and Electrode Placement for Post-Traumatic Tremor Informed consent was obtained from the patient described in Example 1 above prior to the DBS procedure. A high resolution, volumetric, three tesla MRI scan was obtained one day prior to the procedure. On the morning of the procedure, a CRW head ring was applied under local anesthesia and a high-resolution stereotactic head CT scan was obtained. Using software developed at University of Florida, the CT and MR images were fused and stereotactic targeting was carried out using the high quality MR images. The software facilitates navigation in "atlas space" (a three-dimensional, orthogonal Cartesian coordinate system centered on the patient's mid-commissural point), which is readily defined by identifying the anterior and posterior commissures and a non-colinear midline point in the patient's brain.

The target and trajectory were selected in atlas space and the corresponding CRW coordinates were automatically generated and used to set the stereotactic frame. Detailed microelectrode recording confirmed the location of the Vc and VIM thalamic nuclei.

Two Medtronic™ 3387 DBS electrodes (1.5 mm contacts and 1.5 mm spacing between contacts) were then implanted. The first DBS electrode was placed at the anterior border of the left VIM thalamus with the ventral tip positioned on the AC-PC line (ventral border of thalamus). Macrostimulation confirmed high threshold parasthesis of the thumb and fingers. A second DBS electrode was then implanted on a parallel trajectory two millimeters anterior to the first (at the VOA/VOP junction) with the tip approximately 1-2 mm above the AC-PC line (ventral border of thalamus more anterior).

The positions of the two electrodes 10 and 20 implanted in the patient's brain are schematically shown in FIG. 1. Abbreviations of anatomically distinct regions of the human brain shown in FIG. 1 are as follows: Vci: ventralis caudalis; VIM: ventralis intermedius; VOP: ventralis oralis posterior; VOA: ventralis oralis anterior; Cpi: internal capsule; Zi: zona incerta; Stn: subthalamic nucleus.

Example 3

Post-Operative DBS Programming and Clinical Outcomes

Post-operatively, the VIM electrode was first activated and optimized through serial DBS programming sessions. After 2 months of VIM stimulation (with VOA/VOP off), the VOA/VOP stimulator was activated. VIM DBS parameters used were the following: monopolar 2 cathodal, case anodal, 4.1 Volts, 135 Hz, 90 ms; VOP-VOA. DBS parameters were as follows: monopolar 0 cathodal, case anodal, 4.0 Volts, 185 Hz, 90 ms. Standardized tremor and disability rating scales were used to evaluate outcomes over a 6-month period.

Results. Referring to FIG. 2, the patient's tremor was reduced with VIM stimulation alone, but not enough to significantly alter his disability score. With activation of the single electrode, there was a decline in tremor benefit over time, manifested as a tremor rebound after one to two months on VIM stimulation. After two months of VIM stimulation with VOA/VOP off, the VOA/VOP stimulator was activated, at which time the patient experienced a marked and sustained improvement in tremor and disability, up to the end of follow-up at six months (FIG. 2). The patient was able to return to gainful employment.

This case illustrates a new approach for the treatment of patients with Holmes tremor. VIM stimulation is often initially successful in the treatment of patients with Holmes tremor, post-traumatic tremors, and multiple sclerosis tremor; however we and others have observed that over weeks to months the tremor generally rebounds with significant worsening, despite repeated DBS programming sessions. This failure of VIM DBS has led many groups to be reluctant to offer VIM DBS for tremors other than Parkinsonian and essential tremor.

The addition of a second electrode is straightforward from a technical standpoint. The second DBS lead can be placed about 2 mm anterior to the first after microelectrode mapping of the thalamus has identified the location of Vc and VIM. Activation of the second electrode may augment the effectiveness of VIM DBS in patients with these more problematic tremors.

There are several potential mechanisms that may explain Holmes tremor, but the exact pathophysiology remains unclear (Deuschl, G., et al., Muscle Nerve, 2001. 24(6): 716-35). VIM stimulation for the treatment of Holmes tremor is certainly reasonable, considering the benefit that is consistently achieved with this method in the treatment of Parkinsonian tremor and essential tremor (Ondo, W., et al., Neurology, 1998, 51(4):1063-9; Troster, A. I., et al., Brain Cogn, 1998, 38(2):125-49). However, the outcomes of VIM DBS for Holmes tremor have been disappointing. One potential explanation for this reduction in efficacy may be related to differences in tremor mechanism. Holmes tremor may involve more than the cerebello-thalamo-cortical loop, and therefore placement of a lead in VIM may not be enough to address this tremor subtype.

Without intending to be bound by theory, one rationale for placing two electrodes as described above was to affect both the cerebellar receiving area (VIM) and the pallidal receiving area (VOA/VOP), although it is recognized that there is some debate as to whether VOP is also a cerebellar receiving area (Krack, P., et al., Mov Disord, 2002, 17 Suppl 3:S2-8), and Lenz and colleagues have shown tremor-related cells in the region of VOP-VIM (Lenz, F. A., et al., Brain, 1994, 117 (Pt 3):531-43; Lin, Y. C. and F. A. Lenz, Chin Med J (Engl), 1993, 106(5):372-4; Lin, Y. C. and F. A. Lenz, Chin Med J (Engl), 1994, 107(4):265-70).

An alternative explanation for the success of this technique may be related to increasing the effective volume of stimulation. Previous lesion studies by Hirai and colleagues have documented the need to invoke larger lesions for post-traumatic or proximal arm tremors (Hirai, T., et al., Brain, 1983, 106 (Pt 4):1001-18). The need for a larger lesion would imply that whatever the therapy (lesion or DBS), more of the thalamic somatotopy must be affected for maximal benefit in these difficult tremors. The thalamus is somatotopically organized similar to an onion skin (Vitek, J. L., et al., J Neurophysiol, 1994, 71(4):1498-513; Vitek, J. L., et al., J Neurophysiol, 1996, 75(6):2486-95. The shoulder and more proximal body parts have a broad representation on the onion skin, such that it may be difficult to affect both the distal hand and the shoulder with the current field produced from a single DBS electrode. The placement of a second electrode may permit the stimulation to affect more of the thalamic somatotopy.

Several observations support the notion that the mechanisms of Holmes and post-traumatic tremors may differ from those invoked to explain essential tremor. First, some of these tremors are levodopa responsive, especially if high doses of levodopa are used (Berkovic, S. F. and P. F. Bladin, Clin Exp Neurol, 1984, 20:119-28; Velez, M., et al., Mov Disord, 2002, 17(4):741-2; Pezzini, A., et al., Parkinsonism Relat Disord, 2002, 8(3):177-80). In a case of a midbrain tremor, a posteroventral pallidotomy performed after a failed thalamotomy resulted in successful tremor control (Miyagi, Y., et al., J Neurosurg, 1999, 91(5):885-8). Because different mechanisms appear to be involved in these tremors, it follows that different treatment strategies may be needed.

Although the pathophysiology of Holmes tremor remains somewhat unclear, patients with disabling tremor who are refractory to medications may have another option according to the methods of the invention. We are encouraged by the excellent outcome in this patient's case and it has led us to believe that for Holmes tremor, and potentially other difficult to treat tremors such as tremor associated with multiple sclerosis, two or more leads may be preferable to one.

Example 4

Multiple Lead DBS Treatment of Patients with Post-traumatic and Multiple Sclerosis Tremor This Example describes results of the multiple lead technique which was employed in four DBS patients, three with post-traumatic tremor, and one with multiple sclerosis tremor.

Four patients with either post-traumatic tremor (n=3), or multiple sclerosis tremor (n=1) each underwent the placement of two DBS leads (one at the VIM/VOP border and one at the VOA/VOP border), as described in Examples above. Pre-operatively all patients underwent testing with the tremor rating scale (TRS) (off all tremor medications). Patients were then followed for a minimum of six months with TRS scales and ultimately all were retested with the TRS in four conditions: On VIM DBS plus On VOA/VOP DBS, On VIM DBS/ Off VOA/VOP DBS (5 hour DBS washout), Off VIM DBS/ Off VOA/VOP DBS (12 hour overnight washout), and Off VIM DBS/On VOA/VOP DBS (5 hour DBS washout). The conditions were tested off all tremor medications. The order of testing was fixed over two days, and the patient, but not rating clinician, was blinded to the testing conditions.

Surgical Procedures. Informed consent was obtained from each patient prior to the DBS procedure. Surgical procedures were performed essentially as described above. Briefly, a high resolution, volumetric, three tesla MRI scan was obtained one day prior to the procedure. On the morning of the procedure, a CRW head ring was applied under local anesthesia and a high-resolution stereotactic head CT scan was obtained. The CT and MR images were fused and stereotactic targeting was carried out using high quality MR images. The initial target and trajectory were selected in AC-PC space and the corresponding CRW coordinates were automatically generated and used to set the stereotactic frame, as described. Detailed microelectrode recording confirmed the location of the anterior border of ventralis caudalis nucleus (Vc), as well as the sensory and sensorimotor hand regions of Vc and VIM respectively.

Two Medtronic™ 3387 DBS electrodes (1.5 mm contacts and 1.5 mm spacing between contacts) were then implanted. The first DBS electrode was placed 2 mm anterior to the anterior border of Vc (the presumed VIM/VOP junction) with the ventral tip positioned on the AC-PC line (ventral border of thalamus). Macrostimulation was used in all cases to confirm high threshold parasthesias of the thumb and fingers. The second DBS electrode was then implanted on a parallel trajectory two millimeters anterior to the first (at the presumed VOA/VOP junction) with the tip approximately 1-2 mm above the AC-PC line (ventral border of thalamus more anteriorly). The electrodes were placed through a single 14 mm burr hole and were secured using a single Navigus cap, which had been modified to allow the egress of two electrodes.

Post-operatively, programming was accomplished by determining thresholds for side effects and for benefits in each contact on each lead. The VIM impulse generator was programmed first (over an approximate period of several weeks) and maximal clinical benefit was achieved prior to turning on the VOA/VOP lead (which was added at a separate programming session, and then optimized over several weeks). Individual changes in programming were determined by clinical examination in each patient, but all settings were tried for at least four weeks before re-rating with a TRS scale.

Patient demographics from these studies are shown in Table 2A.

TABLE 2A

Patient Demographics

| Patient # | Age | Sex | Tremor Type | Hand | Medications Failed | Years/Tremor | Follow-up |
|---|---|---|---|---|---|---|---|
| 1 | 24 | M | Post-trauma | R | Levodopa, Benzo, Antichol | 16 | 12 |
| 2 | 39 | M | Post-trauma | L | Levodopa, Benzo, Antichol, Beta | 3 | 6 |
| 3 | 30 | F | Multiple Sclerosis | R | Levodopa, Benzo, Antichol, Prim, Relax | 8 | 21 |
| 4 | 18 | F | Post-trauma | R | Levodopa, Benzo, Antichol, DA agon | 4 | 8 |
| Totals | 27.8 | | | | | 7.8 | 11.8 |

Table 2A legend:

Sex - M = male, F = female;

Hand - hand that was treated with contralateral DBS,

Medications - all medications were given in maximally tolerated doses;

Benzo - benzodiazepine,

Antichol - anticholinergic,

Beta = beta blocker,

Prim = primidone,

Relax = muscle relaxant,

DA agon = dopamine agonist;

Year/Tremor = total number of years with tremor;

Follow-up = longest follow-up (in months) where patient received testing in all four conditions as described above.

Table 2B lists the parameters used for DBS stimulation in the patients indicated in Table 2A.

TABLE 2B

Chronic DBS Stimulation Parameters

| Patient # | Location | Mono/Bipolar | Cathode | Anode | Voltage | Pulse Width | Frequency |
|---|---|---|---|---|---|---|---|
| 1 | VIM | Monopolar | 2 | Case | 4.1 | 90 | 185 |
| 1 | VOA/VOP | Monopolar | 0 | Case | 4 | 90 | 185 |
| 2 | VIM | Monopolar | 2 | Case | 3 | 60 | 160 |
| 2 | VOA/VOP | Monopolar | 1 | Case | 3.1 | 60 | 145 |
| 3 | VIM | Bipolar | 0 | 3 | 4 | 120 | 135 |
| 3 | VOA/VOP | Bipolar | 1 | 3 | 5.8 | 90 | 135 |
| 4 | VIM | Bipolar | 2 | 3 | 3.6 | 120 | 185 |
| 4 | VOA/VOP | Bipolar | 2 | 3 | 2.9 | 90 | 135 |

Table 2B legend:
Location - target location being stimulated with chronic DBS,
Pulse Width is represented in microseconds;
the frequency is represented in hertz.

Results: Patient 1 (also described in Examples 1 and 2 above) is a 24-year old man with a 16-year history of unilateral post-traumatic Holmes tremor (low frequency rest, high amplitude postural and high amplitude action tremor) sustained after being hit by a car (pedestrian). He tried maximal doses of levodopa, anticholinergics, and benzodiazepines. The tremor prevented him from holding a job. The tremor improved considerably after VIM plus VOA/VOP DBS, and the patient was able to obtain and hold a job, and felt subjectively the tremor was almost completely resolved.

Patient 2 is a 39-year old man who was hit by a car three years prior to presentation. He developed a left hand post-traumatic Holmes tremor (low frequency rest, high amplitude postural and high amplitude action tremor), along with right upper extremity ataxia, truncal titubation, and gait ataxia. The tremor prevented him from writing or performing dextrous tasks with his left hand. Long term follow-up with VIM plus VOA/VOP DBS revealed the patient's rest and postural tremor resolved, and his action tremor was tremendously improved. He noted that his truncal titubation improved, and his ipsilateral arm tremor also improved. He continued to have gait ataxia, but felt he had tremendous improvement, now being able tie his shoes, handwrite, and drink from the treated hand.

Patient 3 is a 30-year old woman with relapsing remitting multiple sclerosis for 13 years who presented with bilateral severe postural-intention tremors (high amplitude postural-action tremors with a ballistic quality on intention). She had these tremors for eight years prior to presentation. The tremors, particularly her right upper extremity tremor, prevented her from eating, drinking, or operating a wheel chair. Long-term follow-up revealed the patient could handwrite, drink from a cup and operate her motorized wheelchair. She had some mild residual action tremor, but felt she had improved tremendously.

Patient 4 is an 18-year old woman who was thrown from her motor vehicle and had a resulting tremor, i.e., right hand Holmes tremor (low frequency rest, high amplitude postural and high amplitude action tremor) and gait ataxia. The tremor was present for four years. The tremor prevented her from eating, and from handwriting, which impeded her ability to attend college. Follow-up with VIM plus VOA/VOP DBS revealed that her handwriting improved, her tremor resolved, and she was able to attend college.

Table 3 summarizes the baseline and follow-up scores for these four patients.

TABLE 3

Baseline and Follow-up TRS Score Per Condition for Each Patient

| Patient# | Condition | Contralateral UE TRS | | Total TRS Score | | TRS Historical Score | |
|---|---|---|---|---|---|---|---|
| | | Score | % reduction | Score | % reduction | Score | % reduction |
| 1 | Baseline | 6 | — | 26 | — | 16 | — |
| | None | 5 | 16.67 | 22 | 15.38 | — | — |
| | VIM | 5 | 16.67 | 20 | 23.08 | — | — |
| | VOA/VOP | 4 | 33.33 | 19 | 26.92 | — | — |
| | Both On | 3 | 50.00 | 16 | 38.46 | 1 | 93.75 |
| 2 | Baseline | 7 | — | 60 | — | 21 | — |
| | None | 5 | 28.57 | 50 | 16.67 | — | — |
| | VIM | 4 | 42.86 | 36 | 40.00 | — | — |
| | VOA/VOP | 4 | 42.86 | 35 | 41.67 | — | — |
| | Both On | 3 | 57.14 | 31 | 48.33 | 15 | 28.57 |
| 3 | Baseline | 8 | — | 60 | — | 27 | — |
| | None | 6 | 25.00 | 52 | 13.33 | — | — |
| | VIM | 4 | 50.00 | 45 | 25.00 | — | — |
| | VOA/VOP | 3 | 62.50 | 49 | 18.33 | — | — |
| | Both On | 3 | 62.50 | 46 | 23.33 | 26 | 3.70 |
| 4 | Baseline | 6 | — | 42 | — | 27 | — |
| | None | 4 | 33.33 | 30 | 28.57 | — | — |
| | VIM | 3 | 50.00 | 18 | 57.14 | 9 | 66.67 |

TABLE 3-continued

Baseline and Follow-up TRS Score Per Condition for Each Patient

| Patient# | Condition | Contralateral UE TRS | | Total TRS Score | | TRS Historical Score | |
|---|---|---|---|---|---|---|---|
| | | Score | % reduction | Score | % reduction | Score | % reduction |
| | VOA/VOP | 3 | 50.00 | 19 | 54.76 | — | — |
| | Both On | 2 | 66.67 | 14 | 66.67 | 9 | 66.67 |

Table 3 legend:
Contralateral upper extremity score - addition of the rest, postural, and action tremor componenets of the TRS in the treated arm.
None - refers to VIM and VOP DBS off.
Baseline refers to score prior to implantation.
Both On refers to VIM plus VOA/Vop DBS in the on state.
TRS Historical Score represents the total of the items scored based on patient history.
Both - both VIM and VOA/VOP DBS were "on."

As can be seen from Table 3, each of the patients showed improvements in all four conditions when compared to baseline. All of the improvements were maintained with chronic DBS, without tremor rebound. The improvement was smallest in the Off VIM/Off VOA/VOP condition. Three subjects showed the most improvement in the On VIM/On VOA/VOP condition.

Group Analyses. An analysis was performed to determine whether each condition was associated with significant tremor reduction (percentage change). Referring to Table 4, the results showed that the percentage reduction was significant for each condition and measure (all t's>4.40; all p's<0.023), despite the small number of participants (Table 4). The percentage reduction was significant in the Off VIM/Off VOA-VOP condition.

TABLE 4

Percentage Reduction (Compared to 0) for Each Condition and Measure

| | Condition | Mean % reduction |
|---|---|---|
| Contralateral Upper Extremity | None (Both off) | 25.89 |
| | VIM On | 39.88 |
| | VOA/VOP On | 47.17 |
| | Both On | 59.08 |
| Clinical (TRS) | None (Both off) | 18.49 |
| | VIM On | 36.31 |
| | VOA/VOP On | 35.42 |
| | Both On | 44.20 |

Table 4 legend:
Both-refers to VIM plus VOA/VOP DBS

Differences were then examined between conditions, including: (1) Off VIM/Off VOA/VOP versus the other conditions, (2) On VIM versus On VOA/VOP, (3) On VIM plus On VOA/VOP versus On VIM, (4) On VIM versus On VOA/VOP. For the contralateral upper extremity, the Off VIM/Off VOA/VOP yielded less symptom reduction (percentage) than all three other conditions. For the total TRS score, the Off VIM/Off VOA/VOP yielded less symptom reduction than the On VOA/VOP condition, and On VIM plus On VOA/VOP condition. There was improvement when comparing the difference between the Off VIM/Off VOA/VOP and On VIM. The On VIM and On VOA/VOP conditions did not differ from each other in terms of contralateral upper extremity symptoms (percentage reduction), or total TRS score. The On VIM plus On VOA/VOP condition showed greater symptom reduction than the On VIM condition for contralateral upper extremity, but not total TRS score. Compared to the On VOA/VOP condition, the On VIM plus On VOA/VOP condition showed greater symptom reduction for total TRS score, and a trend toward greater symptom reduction for the contralateral upper extremity score.

Group Analyses of Condition Effects. The average contralateral upper extremity symptom score and total clinical score (TRS) for each condition was first calculated using the average score within each participant (separately), and then averaging across participants. Because of the small number of participants in our study, using participants' averages would have resulted in low power. We therefore conducted our analyses (results shown in Table 5) by considering all the separate observations of the same condition as individual data, including subject as a covariate dummy variable to account for the fact that the four patients showed very different levels of symptom severity throughout the course of treatment. Because it was found that time generally did not contribute to severity of symptoms (with one exception), it was not included as a covariate.

TABLE 5

Descriptive Statistics for the Four Conditions

| | Contralateral TRS UE | | Clinical (Total TRS) | |
|---|---|---|---|---|
| Condition | Mean | SD | Mean | SD |
| None (Both Off) | 5.06 | 0.77 | 38.38 | 15.69 |
| VIM | 4.02 | 0.85 | 31.00 | 15.36 |
| VOA/VOP | 3.75 | 0.65 | 30.88 | 15.45 |
| Both On | 2.94 | 0.49 | 27.61 | 16.28 |

Table 5 legend:
Both-refers to VIM plus VOA/VOP DBS;
contralateral TRS score refers to the total of rest, postural and action tremor scores in the treated extremity.

Referring to Table 5, results of these analyses showed that the effect of condition was significant for contralateral upper extremity symptoms, $F(3, 51)=10.24$, $p<0.001$, and overall TRS score, $F(3, 51)=8.92$, $p<0.001$. Planned contrasts for contralateral upper extremity symptoms and overall TRS score showed that the Off VIM plus Off VOA/VOP condition yielded significantly worse scores than all three other conditions when considering both contralateral upper extremity symptoms, all $p$'s<0.02, and overall TRS score, all $p$'s<0.03. The on VIM and on VOA/VOP conditions did not significantly differ in terms of contralateral upper extremity symptoms, $F(1,17)=0.36$, $p>0.55$, or overall clinical score, $F(1,17)=0.02$, $p>0.88$. The on VIM condition differed significantly from the on VIM plus on VOA/VOP condition for contralateral upper extremity symptoms, $F(1,39)=8.0$, $p<0.008$, and overall TRS score, $F(1,39)=8.34$, $p<0.07$. The on VOA/VOP condition did not significantly differ from the on VIM plus on VOA/VOP condition for contralateral upper extremity symptoms, $F(1,29)=3.0$, $p>0.096$, and there was only a trend toward a significant difference for overall clinical score, $F(1,29)=4.2$, $p=0.05$. These results, however, should be interpreted with caution as there were few observations (6) for the VOA/VOP condition, and an examination of the means in Table 3 suggests that the scores for this condition were very similar to those obtained for the VIM-on condition.

The results of this study revealed that treatment utilizing a double lead technique was effective in all four conditions tested (at a minimum of six months follow-up). The Off VIM plus Off VOA/VOP condition, showed improvement compared to baseline in both contralateral upper extremity symptoms and total TRS score. Without intending to be bound to theory, it is believed that although this condition (two leads in place but in the Off condition) yielded less symptom reduction than the others, its benefits suggest one or a combination of the following possibilities, including: the effects of the DBS were cumulative over time (chronic positive effect from continuous stimulation); there was a significant and sustained collision or microthalamotomy effect from the two leads; or there was a significant placebo effect. The On VIM and On VOA/VOP conditions did not differ, but there was some evidence, when considering all the observations, that the condition both leads On yielded increased symptom reduction. The procedure was safe in these four patients, and the follow-up programming was not difficult or excessively time-consuming.

Example 5

Clinical Trial Methods for Multiple Lead DBS Therapy for Tremor Patients

This Example describes protocols for conducting large scale, long-term testing of the multiple lead DBS method in clinical populations having post-traumatic or multiple sclerosis tremor.

Figure 3:
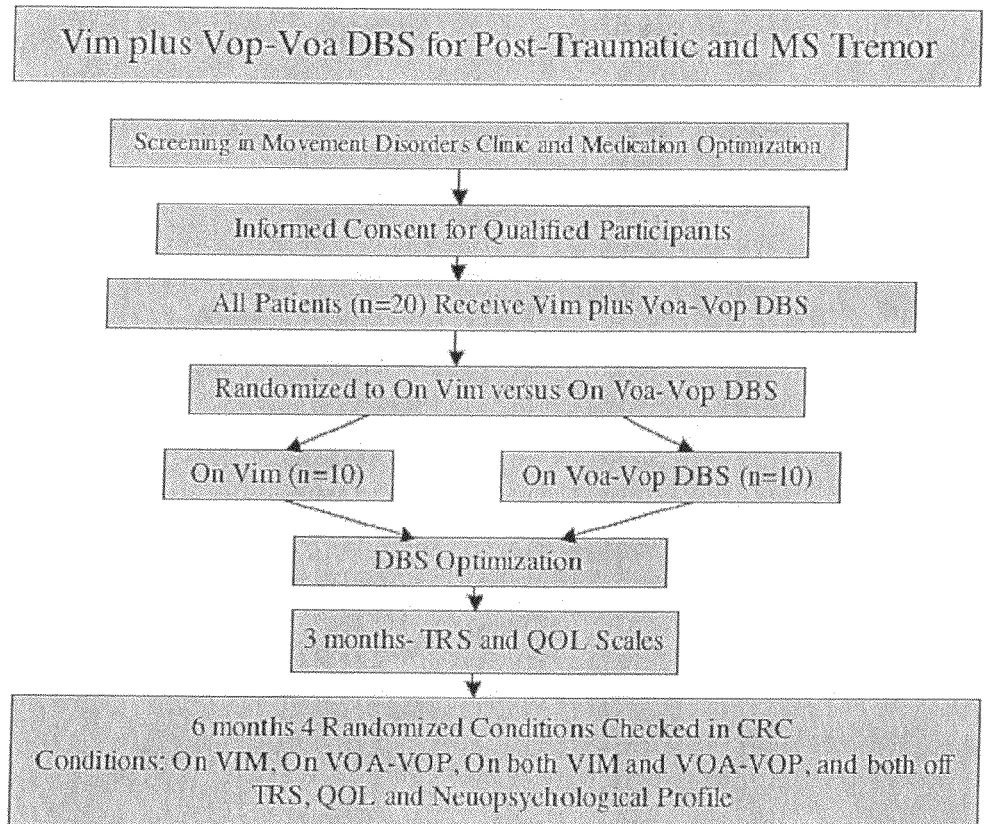
FIG. 3 is a flow chart showing steps in the treatment of subjects receiving DBS multiple electrode therapy for tremor, according to an embodiment of the invention.

The overall design of the study is shown in the flow chart in FIG. 3. As described in further detail below, the flow chart illustrates the sequence of events regarding evaluation, randomization, implantation, and follow-up evaluations for patients in the clinical study. Referring to FIG. 3, after the first baseline visit, patients are randomized to receive an "On VIM" or "On VOA/VOP" condition stimulation for the first 3 months of the study. Within one month following their baseline visit and randomization, they receive surgery for implantation of two DBS devices (implanted into VIM and VOA/VOP). At the DBS optimization following the 3-month visit, both electrodes are activated on all patients. Over the next five and a half months, medications are adjusted in conjunction with optimization of the device to provide the best possible control of tremor symptoms. Medications and device adjustments are not made for two weeks prior to the 3- and 6-month follow-up examinations.

Clinical Trial Design and Methods:

1. Patient Recruitment

A total of 20 patients with either post-traumatic or multiple sclerosis tremor is enrolled in this study. Patients are drawn from the Movement Disorders Center at the University of Florida (UFMDC), a regional referral center for complex medical care, treating patients representing virtually every state, the majority of whom are from Georgia, Alabama, Florida, and South Carolina.

Patient demographics indicate that the incidence of multiple sclerosis and post-traumatic tremor is approximately equal between males and females, and affects people of all ethnic backgrounds. The human subject population for this clinical trial is representative of the general incidence of these movement disorders throughout the Southeastern United States Region. Representative enrollment in the study is shown in Table 6.

TABLE 6

STUDY ENROLLMENT: Number of Subjects

| | Sex/Gender | | |
|---|---|---|---|
| | Females | Males | Total |
| Ethnic Category | | | |
| Hispanic or Latino | 1 | 1 | 2 |
| Not Hispanic or Latino | 9 | 9 | 18 |
| Ethnic Category Total of All Subjects* | 10 | 10 | 20 |
| Racial Categories | | | |
| American Indian/Alaska Native | | | |
| Asian | | | |
| Native Hawaiian or Other Pacific Islander | | | |
| Black or African American | 1 | 1 | 2 |
| White | 9 | 9 | 18 |
| Racial Categories: Total of All Subjects* | 10 | 10 | 20 |

Table 6 legend:
*The "Ethnic Category Total of All Subjects" must be equal to the "Racial Categories Total of All Subjects." Hispanics are included in the "White" category.

2. Patient Selection

Each patient referred for surgical therapy is evaluated by a neurologist specialized in movement disorders, to confirm the diagnosis of post-traumatic or multiple sclerosis tremor and to be certain that all medical therapies have been optimized. An MRI is obtained if a recent one (within 1 year) is not available for review. The options for surgical therapy, i.e., standard deep brain stimulation of the VIM thalamus, thalamotomy, or multiple electrode thalamic stimulation protocol are explained to patients who are judged to be medically and neurologically suitable for surgery (see inclusion and exclusion criteria, infra). Those patients who choose to participate in the study are evaluated by a psychiatrist, and undergo neuropsychological testing for an assessment of psychiatric and neuropsychological function. If the patient meets eligibility criteria and consents to randomization, he or she is enrolled in the study (see Patient Flow Chart, FIG. 3).

Patients from all ethnic groups with tremor who meet the inclusion criteria and are able to return for follow-up examination are enrolled in the study. There are no groups which are excluded due to sex, race, or ethnicity. The study includes children because post-traumatic tremors often occur under the age of 18. We have performed DBS safely on patients as young as 10 years of age, particularly with generalized dystonia. Concerns about DBS in children include safety, feasibility and patient growth. We have demonstrated safety and feasibility with only slightly modified methodology. The skull is fully grown at age 9, and extension cables are used to allow for increasing height. Children should not be excluded from this study, since children often suffer the catastrophic consequences of post-traumatic and multiple sclerosis tremors.

2.1. Inclusion Criteria a. A clinical diagnosis of disabling post-traumatic tremor or multiple sclerosis tremor [47] is required. The diagnosis is based upon the presence of severe rest, postural, or action tremor (or a combination thereof) that has resulted from trauma or from multiple sclerosis. Since the diagnostic criteria are not validated for post-traumatic and multiple sclerosis tremor, the study relies on the expert diagnosis of a movement disorders neurologist.

b. Age between 10 and 79 years.

c. Unsatisfactory clinical response to maximal medical therapy, with trials of both higher and lower doses of anticholinergics, muscle relaxants, benzodiazepines and levodopa drugs.

d. A stable, optimized medical regimen of drug therapy for at least one month prior to surgery.

Recruitment is restricted to patients who agree to return on an as needed basis for reprogramming and scheduled follow-up evaluations.

2.2 Exclusion Criteria a. Clinically significant medical disease that would excessively increase the risk of developing peri-operative complications (e.g., significant cardiac or pulmonary disease, uncontrolled hypertension, inadequately treated major depression).

b. More than mild cerebellar dysfunction (as judged by an expert movement disorders neurologist) in the arm being considered for therapy.

c. Evidence of secondary or atypical movement disorder as suggested by the presence of any of the following: 1) history of stroke(s); 2) exposure to toxins or neuroleptics; 3) history of encephalitis; 4) neurological signs of upper motor neuron disease, moderate/severe cerebellar involvement, supranuclear gaze palsy, or significant orthostatic hypotension.

d. MRI scan with significant evidence of severe brain atrophy or other prohibitive abnormalities (e.g., absence of a thalamic target for DBS, lacunar infarcts, or iron deposits in the putamen).

e. Dementia as evidenced by impairment in two neuropsychological domains and impaired or borderline neuropsychological function in one additional domain. This criterion is based on the recommendations of Bornstein for assessing dementia in Parkinson's disease [48]. Such patients are excluded because significant dementia can compromise the ability of patients to accurately assess the impact of DBS. Patients with dementia are more likely to develop hallucinations or delusions, as well as develop other physical problems such as incontinence and infections that may affect the motor aspects of the movement disorder, as well as influence the specialists' ability to evaluate them. Furthermore, in such cases, follow-up in patients is likely to be difficult given the associated problems with transportation and the high levels of caregiver stress present in such situations. The Mattis Dementia Rating Scale [49, 50] is used to assess the level of intellectual function. Patients are excluded with scores reflecting clinical dementia (with some latitude given, because post-traumatic cases tend to have other cognitive dysfunction; i.e., the reason we lower the criteria to 110 (<110)).

f. A major psychiatric disorder on the Structured Clinical Interview for DSM-IV (SCID-IV) [51]. Patients who meet criteria for current Major Depression or Major Depression within 3 months of entry into the study are excluded. The SCID-IV uses standardized criteria to diagnose all current and past psychiatric diagnoses by DSM-IV criteria. High rates of psychiatric co-morbidity can complicate any neurosurgical clinical trial. While the optimal study might exclude any patient with psychopathology, we do not believe this is realistic or practical, given that the majority of patients with advanced movement disorders will suffer from some degree of anxiety or depression. We therefore screen patients for psychiatric disorders, treat the disorders prior to DBS and admit into the study patients who are psychiatrically stable for at least three months prior to entry (e.g., without an active psychiatric diagnosis by SCID criteria).

3. Comprehensive Psychiatry Screening Prior to Baseline

A psychiatrist provides a comprehensive psychiatric evaluation of all candidates during a screening period before other baseline assessments. Clinically significant depression, anxiety and psychosis are treated before patients enter the baseline assessment period. This treatment minimizes the potentially confounding impact of psychiatric symptoms on physical and neuropsychological outcome. This also minimizes the chances of post-surgery depression or anxiety requiring new psychotropic medication.

Treatment methods are selected by a physician with extensive clinical experience in the assessment and treatment of psychiatric problems in patients with movement disorders. Based upon previous experience and the literature, treatments include antidepressant medications (primarily the serotonin re-uptake inhibitors), anxiolytics (primarily lorazepam and clonazepam) or antipsychotics, which have minimal extrapyramidal side effects (risperidone, olanzipine or clozapine). In our experience, the presence of psychiatric syndromes in movement disorders, with the exception of depression, is generally recognized and treated by the referring physician and the majority of patients meet the psychiatric screening criteria prior to study screening.

4. Informed Consent

Subjects are fully informed of the nature of the study and of all of their options for treatment, as described above, at the time of their initial screening. To be enrolled in the study they are required to sign a consent form that includes a full description of the testing protocols and of the operative procedures when appropriate. In addition, all treatment options available to patients are discussed. Each patient is provided with any new information concerning treatment options as it becomes available, in order to give the patient the ability to make the most informed decision possible.

5. Drug Management/DBS Programming

All patients are first optimized on movement disorders medications and maintained on a stable dose for at least one month prior to their baseline visit for the study. Following surgery, medications are adjusted in concert with optimization of the DBS parameters, to provide optimal control of motor signs. Medication adjustments and programming of the Soletra™ pulse generator is performed as necessary up to two weeks prior to the 6-month postoperative visit, after which no further adjustments are made in either the medication or stimulation parameters until after the 6-month postoperative assessment.

6. Randomization and Blinded Assessment

All patients receive VIM plus VOA/VOP DBS (2 electrodes). Patients are randomized to one of two surgical groups ("On VIM" or "On VOA/VOP") using standard methods of the General Clinical Research Center's Data Services Laboratory (DSL), as shown in FIG. 3. They undergo blinded assessment of their condition at 3 months, with the tremor rating scale score (TRS) and Quality of Life measure. After this visit, both devices are turned on and optimized in all patients, who return for a six-month evaluation of all conditions. These conditions are also randomized using standard methods of the DSL under conditions as follows: "On VIM," "On VOA/VOP," "On VIM and VOA/VOP," and "both Off"). The surgical team is not involved in the preoperative and 3- and 6-month postoperative evaluations. Pre-operative and post-operative examiners for the study are blinded as to the site of stimulation. In addition, every effort is made to blind the patients as to the site of stimulation by not openly discussing the names of the structures being mapped in the operating room (since patients are awake during implantation), and by discussing all potential side effects associated with DBS stimulation preoperatively (whether related to VIM or VOA/VOP).

7. Pre-Surgical Baseline Evaluation

The pre-surgical evaluation includes screening of mood, neuropsychological, and motor systems. The tests are selected based on the results of data, e.g., as shown in Examples 3 and 4, and the current DBS literature. Total estimated testing time is about 40 minutes.

7.1 Mood Battery

The mood battery includes the following tests:

a. Visual Analog Mood Scale (VAMS) [52]. The VAMS is an excellent test to study mood specifically in patients with neurodegenerative diseases. Most standardized measures of mood are not appropriate for this population; however the VAMS are valid, standardized measures developed specifically for neurologically impaired patients. The VAMS assess eight moods: sad, happy, tense, afraid, tired, energetic, confused, and angry.

b. Profile of Mood States (POMS). The POMS assesses six subjective subscales: tension-anxiety, depression-dejection, anger-hostility, fatigue-inertia, vigor-activity, and confusion-bewilderment. The POMS analysis is added to the VAMS to ensure correlation of mood changes [53]. In addition, this subjective subscale is added because studies with patients show that observations of mood by the examiner are significant and correlated with the VAMS.

c. Spielberger State-Trait Anger Expression Inventory (STAXI). The STAXI, a validated scale of patient reported anger, is added to the VAMS and POMS to more carefully characterize anger in the patients.

d. Beck Depression Inventory (BDI) [54-56]. In addition to the above instruments, we use a well-established instrument to study depression. The BDI scale measures the physical symptoms, vegetative symptoms, and somatic symptoms of patients, and in addition contains a 13-item cognitive and affective subscale to estimate the level of depression. The physical, vegetative, and somatic complaints are analyzed separately from the cognitive and affective scales, since the former can be more affected by physical symptoms and somatic complaints resulting from surgery, and therefore can be overestimated.

7.2 Neuropsychological Battery

The neuropsychological battery focuses on measures sensitive to attention, frontal lobe function and working memory. In our patient studies and in reports of others, frontal lobe measures have been sensitive to neuropsychological change following surgical treatments for movement disorders. We also include other tests of non-frontal lobe function, which have shown changes both in the literature and in our studies. These tests provide a comparison for correlation, and in addition balance out the short battery. Because of the need for the tests to be administered in four conditions (at the 6-month follow-up), equivalent forms for each test are produced, and the battery is designed to be short, in order to minimize practice effects and testing fatigue. The following tests are performed:

a. Stroop Color Word Naming Test. The Stroop Naming Test requires naming of the color of ink of colored words (green, blue, red) that are printed in incongruent ink. The test measures the ability to maintain attention focused on the attribute of the colored words (ink) and ignore the meaning of colored words while naming the colors. It is a test of frontal lobe function [57].

b. Letter and Category Fluency Tasks. In the Letter Fluency test, subjects are asked to produce words beginning with a particular letter, excluding proper nouns and the same word with a different suffix. The semantic version of this test, Category Fluency, requires the subject to produce nouns belonging to a specific category. Both Letter and Category Fluency are tests of frontal lobe function and require initiation and maintenance of behavior.

c. Hopkins Verbal Learning Test (HVLT). The HVLT is a verbal memory test in which patients are asked to recall words from lists that are read to them. There is a recognition and delayed recall component to this task. The HVLT requires use of both working and episodic memory.

d. Subject Ordered Pointing Task (SOP). The SOP task requires that patients point to a picture or design on a card filled with multiple panels, each with different pictures or designs. The subject is then shown a series of cards and asked to point to a different design on each. He or she is scored by errors, and number of attempts until the first error. The test assesses working memory [58].

e. Paced Auditory Serial Addition Test (PASAT) In the PASAT, patients must listen to pre-recorded number sequences and perform serial addition tasks as requested by the examiner, requiring the ability to sustain attention and use working memory. The PASAT is added to our battery because it is a useful test for assessing problems with attention, and it allows assessment of sustained attention, which has been observed to improve with DBS [59].

7.3 Voice and Speech Evaluations

Voice and speech are evaluated using four types of stimuli and two methods of analysis. The stimuli are: vowel prolongation, diadochokinesis, sentence intelligibility, and aloud reading of the Grandfather Passage (Darley, Aronson, and Brown, 1975). The two types of analysis are perceptual and acoustic.

a. Vowel Prolongation. Each participant is instructed to take as large a breath as possible and then produce an "a" sound of consistent quality and intensity for as long as possible. Two such productions are elicited and recorded via digital tape recorder and head mounted microphone in a standardized position. Testing is done in quiet. Acoustic analysis is completed to quantify presence of tremor and voice quality. Voice quality is derived from the vowel format structure.

b. Diadochokinesis. Each participant is instructed to repeat a series of "puhs," "tuhs," and "kuhs" at four per second and as fast as possible, while striving to keep them even and crisp. Two trials on each of the three are completed. Recording is the same as for the vowel and acoustic analysis and yields the number and variability in intensity and timing of each.

c. Intelligibility. Intelligibility is tested using two measures.

1. Sentence Intelligibility Test (SIT). The SIT (Yorkston, Beukelman, & Tice, 1996) is a computerized version of the Assessment of Intelligibility in Dysarthric Speakers (AIDS) (Yorkston et al., 1984). The SIT and the AIDS tests have standardized methodology, validity, and reliability. The methodology of the SIT requires that an individual read aloud the sentences seen on a computer screen, making this a measure of connected speech intelligibility elicited by reading, rather than a spontaneous speech task.

2. Spontaneous Speech Intelligibility Measure (SSI). Research has demonstrated that a speech intelligibility measure based on a reading sample resulted in significantly different scores than those derived from spontaneous speech samples of individuals with the dysarthria of Parkinson's disease (Kempler & Van Lancker, 2002). In addition, because spontaneous speech is the standard in communicative interactions, and the "ideal" outcome of therapy, we determined that a sample of spontaneous speech would add important information to the study, in addition to a measure of sentence intelligibility. Accordingly, a one-minute spontaneous speech sample, asking the subject to describe the place where he/she was born, is collected.

7.4 Motor Battery a. The Tremor Rating Scale (TRS) [51]. The TRS is the same rating scale used by most movement disorders neurologists to rate tremor. We believe this to be an adequate tool, and it has previously been used in a Medtronic™ study to assess efficacy of DBS in essential tremor for the FDA.

b. Videotape Assessment. Standardized videotape assessments of the TRS are performed at baseline, at 3 months, and at the 6-month follow-up visit under each of the four conditions, to allow results to be independently validated by other blinded raters.

8. Assessment of Electrode Location

As discussed, high resolution, volumetric MR images are acquired prior to implantation of the DBS electrode. Additionally, thin cut, volumetric CT is acquired approximately one month after electrode implantation. This delay is intended to allow correction of any brain shift associated with the implantation procedure. The post-operative CT is then fused with very high fidelity to the pre-operative MRI. The mean and window of the CT images are adjusted to minimize metal artifact, and the position of the electrode relative to the mid-commissural point is carefully measured on magnified images. The position of the electrode is then automatically projected onto the fused pre-operative MR images. Stereotactic coordinates of any designated point on the CT or MRI (e.g., the center of the deepest contact) are generated automatically by the software when the anterior commissure, posterior commissure, and a noncolinear midline point are designated on the MRI. These stereotactic coordinates may then be projected onto a standard brain atlas for comparison.

9. Surgical Procedures a. Stereotactic Localization. The procedure followed for image-guided, stereotactic targeting is as follows, and essentially as described in Examples above. Informed consent is obtained from each patient prior to the DBS procedure. A high resolution, volumetric, three tesla MRI scan is obtained one day prior to the procedure. On the morning of the surgery, a CRW head ring is applied under local anesthesia and a high-resolution stereotactic head CT scan is obtained. Using software as described above, the CT and MR images are fused, and stereotactic targeting is carried out using the high quality MR images. As discussed, the software facilitates navigation in "AC-PC space" (a computationally reformatted MRI with a three-dimensional, orthogonal Cartesian coordinate system centered on the patient's mid-commissural point), which is readily defined by identifying the anterior and posterior commissures and a non-colinear midline point in the patient's brain. The initial target and trajectory are selected in AC-PC space and the corresponding CRW coordinates are automatically generated and used to set the stereotactic frame. Detailed microelectrode recording confirms the location of the anterior border of ventralis caudalis nucleus (Vc), as well as the sensory and sensorimotor hand regions of Vc and VIM, respectively.

Two DBS electrodes (e.g., Medtronic™ 3387 DBS electrodes with 1.5 mm contacts and 1.5 mm spacing between contacts) are then implanted. The first electrode is placed about 2 mm anterior to the anterior border of Vc (the presumed VIM/VOP junction), with the ventral tip positioned on the AC-PC line (ventral border of thalamus). Macrostimulation is used to confirm high threshold parasthesias of the thumb and fingers. The second DBS electrode is then implanted on a parallel trajectory, about two millimeters anterior to the first (at the presumed VOA/VOP junction), with the tip approximately 1-2 mm above the AC-PC line (ventral border of thalamus more anteriorly). The electrodes are placed through a single 14 mm burr hole and are secured using a single Navigus cap, modified to allow the egress of two electrodes.

b. Intraoperative Physiologic Mapping of the Thalamus and Electrode Placement.

Detailed microelectrode recording is used to define the sensorimotor portion of the thalamus. The mapping procedure for the pallidum and thalamus has been described previously [71-73]. Briefly, physiologic maps of the basal ganglia and adjacent structures, i.e., the sensory nucleus and internal capsule, are developed using microelectrode recording to identify the different portions of the basal ganglia by their distinctive patterns of spontaneous neuronal activity. The sensorimotor portion of thalamus is further delineated by the identification of cells whose discharge rate is modulated by active or passive movement.

Electrical stimulation, first with the microelectrode and subsequently with the DBS electrode, is used to further confirm the location of the corticospinal tracts. The DBS electrode is placed within the sensorimotor portion of the thalamus, at approximately lateral 13.5-15 mm, based upon the Schaltenbrand and Bailey Atlas, (the same region that is lesioned in patients undergoing thalamotomy). One of the goals of microelectrode recording is to clearly define the hand region and the anterior border of the Vc. As discussed, the electrode is implanted about 2 mm anterior to the Vc border at the VIM/VOP border. The second electrode is then implanted about 2 mm anterior to the first, at the VOA/VOP border. Motor and sensory stimuli can be used to enhance localization as well because the Vc contains cells that respond to light and deep touch, VIM cells respond to passive movement, and VOA/VOP cells respond to active movement. In addition, the thalamus is somatotopically organized with the face and arm more medial and the leg more lateral. Microelectrode recording and macrostimulation help to define these regions.

Following microelectrode recording and implantation of the DBS electrode(s), macrostimulation is performed using a temporary external pulse generator. A screening protocol is conducted to assess the effect of DBS on tremor, and to ensure that there are no associated side effects that would preclude increasing the voltage to levels necessary to produce an optimal therapeutic effect. In the thalamus, these could include a capsular response if the electrode is placed too far laterally, or the development of parasthesias if the electrode is placed too far posteriorly.

The screening protocol takes approximately 30-45 minutes and includes trials of different electrode combinations at different voltages. Generally, pulse durations of 60-90 ms and frequencies of 130-185 Hz are used. Each contact is then used as the cathode, to assess efficacy and to determine that the electrode is operational. Improvement in tremor and lack of side effects at voltages <3-4 volts are considered indicative of good electrode placement.

10. Postoperative DBS Programming

To program the stimulator we begin with a frequency of about 135 Hz and pulse width of about 60 ms. These parameters are ones commonly used by centers currently performing DBS. Each electrode contact is tested using monopolar stimulation with the contact as the cathode, and the case (Soletra™ or Kinetra™) as the anode. The voltage is then increased in intervals while assessing the patient for improvement in tremor.

Various electrode combinations, i.e., bipolar stimulation, frequencies and pulse durations are used to maximize the clinical benefit while minimizing any potential side effects. Patients are programmed one month after electrode implantation, and adjustments to stimulation and medication in order to optimize motor benefit are made up to two weeks before the 3- and 6-month evaluations. Efforts are made to optimize stimulation and medications prior to mood and neuropsychological evaluations at 6 months.

11. Postoperative Evaluations a. Three Months After Implantation. At this time, TRS scales and quality of life (MOS-36) are assessed.

b. Six Months After Implantation. On their optimized DBS settings, at 6 months, patients undergo repeat TRS, mood, neuropsychological, speech and motor battery testing, identical to the baseline testing, in all four conditions of stimulation (i.e., On VIM, On VOA/VOP, On VIM and VOA/VOP, and both Off in random order. (See flow chart, FIG. 3.) The MOS-36 is also repeated to assess quality of life.

c. Timing and State of Testing. The majority of postoperative testing is performed 6 months after surgery, to assure that effects on mood and cognition from the surgical procedure have stabilized, and to allow time for optimization of DBS programming. Testing at the 6-month follow-up occurs off medications (12 hours prior to testing) and on stimulation. The four random testing conditions are chosen by a computer-generated random sequence and are set by a DBS programmer. Other investigators are blind to the sequence of conditions. The DBS programmer sets the device at each of the four conditions, and the cognitive technician and blinded motor examiner perform their respective evaluations. The conditions are set the night prior and medications are discontinued. Testing occurs, e.g., at about 9 o'clock in the morning, with insurance that the settings have been constant for a minimum of about 12 hours prior to each round of testing. Patients remain blind to the changes.

d. Testing Longer-Term Effects of Stimulation. Patients are followed with a TRS at one year postoperatively, and each subsequent year, as appropriate.

12. Statistical Considerations and Sample Size Determination

One analysis compares 6-month TRS score with both VIM and VOA/VOP stimulators activated to the pre-operative baseline TRS score by the exact Wilcoxon Sign-Rank test [69]. Since the results are discrete distributions, a normality assumption needed for the classical t-test is not considered viable. Based on the studies described herein, two alternative distributions are as shown in Table 6. For each distribution, a simulation study of 10,000 replications was conducted with 20 simulated patients per run. The power of the exact two-sided test at P=0.05 was 91% for Distribution #1 and 82% for distribution #2 (Table 7).

TABLE 7

Statistical Distributions

| Change in TRS Score (Baseline-6 Month) | Distribution #1 (Strong effect) | Distribution #2 (Moderate effect) |
|---|---|---|
| −1 | 20% | 15% |
| 0 | 20% | 40% |
| +1 | 20% | 15% |
| +2 | 20% | 15% |
| +3 | 20% | 15% |

Quality of Life (QOL) is analyzed in the identical fashion as a secondary variable. As it is important to quantify the improvement as well as determine its significance, we obtain a non-parametric approximate 95% two-sided confidence interval for the percentage change from baseline in TRS score and in QOL score as follows. We are at least 96% confident that the true target population percent change lies between the 5th largest (excluding ties) and the 15th largest (excluding ties) of a sample of 20 independent percent change measures.

Side effect profiles are compared through descriptive statistics and non-parametric tests (e.g., Sign-Rank test [70] for one sample and Wilcoxon test [69] for two samples).

For other secondary analyses, the 6-month TRS scores are compared for the short-term effects of turning off none, one, or both electrodes using the Sign-Rank (matched pair approach).

13. Data Entry and Management

Data entry, management and analysis are coordinated by a data manager.

a. Forms and Data Collection. Data forms are designed to capture all primary and secondary outcome data. Each form is complete with a description of how the form is to be completed and scored, as well as when and where it should be completed. The study coordinator ensures that co-investigators have forms available at all times, i.e., copies made from the master set. After co-investigators complete a patient evaluation, they review forms for accuracy and legitimacy of responses. Once completed, the forms are turned in to the study coordinator. The data entry personnel, on a weekly basis, create photocopies of the forms. The original forms are maintained, by patient ID and code of study visits, by the study coordinator and the photocopies are maintained separately by a data manager for safety and quality control purposes.

b. Data Entry. The data is entered into a database, e.g., created in Access. Once initial data entry is complete, the data is entered a second time. This validation ensures accurate and complete data sets. After validation has been completed, the data is exported into a statistical analysis package, e.g., SAS. The permanent data files are maintained by the data manager and may be accessed by biostatisticians and the data manager for analysis.

c. Data Storage and Security. Personal computers where data entry takes place are maintained in locked offices. All modifications to the data files are recorded by the data manager in the SAS software that stores the files. Duplicates of the study data are generated weekly and stored on diskette by a biostatistician and on a secure server for safety purposes, e.g., in the event of a computer hardware failure.

d. Randomization. A randomization list in which the sequence of randomized allocation to "on VIM" or "on VOA/VOP" for the first 3 months of the study, and the randomization of conditions for all patients at 6 months (Conditions: On VIM, On VOA/VOP, On VIM and VOA/VOP, and both Off) is maintained. Treatment allocation occurs when a patient is eligible for the study and the consent for randomization has been obtained. The study coordinator calls the data manager for the randomly assigned state one day prior to surgery. Since primary analyses observe the intent-to-treat principal, it is imperative that every precaution be taken to ensure that the randomization scheme is followed strictly. Baseline information is entered into the database following randomization.

14. Risk Assessment

The risks associated with placement of thalamic DBS electrodes are in general similar to those of any stereotactic procedure, e.g., hemorrhage, infection, seizures, and stroke with motor, sensory, language, and cognitive impairment. The incidence of significant morbidity or death is less than 3-4% [60-67]. The use of microelectrode mapping of the thalamic area prior to introduction of the DBS electrode adds to the total duration of the procedure (approximately 30 minutes/track) and potentially to the risk of hemorrhage because of the microelectrode tracks. The hemorrhage risk associated with microelectrode recording is, however, extremely low based on our experience and the published experience in humans undergoing microelectrode-guided thalamotomy [68] and thalamic DBS. The risk of DBS is generally less than that associated with ablative procedures, since the side effects of DBS are reversible. Generally DBS-associated side effects are transient.

Other potential risks to the patients include: persistent pain at the site of electrode implantation and/or the implantable pulse generator (IPG); seroma or fluid collection or swelling at the IPG site; IPG migration or skin erosion over the IPG or over connector sites; intracranial hemorrhage; infection; cerebrospinal fluid leak; mechanical failure of the system leading to cessation of stimulation or intermittent stimulation. Overall these risks are generally small and the likelihood of any persistent morbidity is considered less than 5%. In addition, during stimulation of the thalamus, patients may experience abnormal involuntary movements, pulling or parasthesias. These are reversible and generally resolve following an adjustment in stimulation parameters. Implanting a second electrode is expected to increase the incidence of side effects only to a modest degree. We believe the incidence of significant adverse events should remain very low even with dual electrode implantation, and we have observed no adverse effects in our study patients.

The clinical cases described in the Examples above illustrate a promising new approach for the treatment of patients with post-traumatic tremor and multiple sclerosis tremor. As discussed above, VIM stimulation is often initially successful in the treatment of patients with Holmes tremor, post-traumatic tremors, and multiple sclerosis tremor, but over weeks to months, the tremor commonly rebounds with significant worsening despite repeated DBS programming sessions. A recent analysis of one large retrospective series of patients who had functional neurosurgical procedures to address post-traumatic tremor revealed that although patients improved significantly, disability scales decreased by only 20% (Krauss et al., J. Neurosurg, 1994, 80(5): 810-819). This lack of efficacy data, as well as reports of failure of VIM DBS monotherapy, has led many groups to be reluctant to offer therapy for these types of tremors. Based on the results shown herein, we conclude that use of the multiple lead DBS procedure could greatly benefit significant numbers of patients with movement disorders such as post-traumatic or multiple sclerosis tremor.

REFERENCES

In some instances, the foregoing text includes numbered citations. The numbers correspond to the references shown below. It is believed that a review of the following references will increase appreciation of the present invention. The contents of all patents, patent applications, and references cited throughout this specification are hereby incorporated by reference in their entireties.

1. Balas I, Llumiguano C, Horvath Z, Kover F, Doczi T. Stereotactic thalamotomy for Parkinsonian and others types of tremor. Experiences of thalamic multiunit burst activity by means of semimicroelectrode. Rev Neurol 2001; 32:520-4.
2. Benabid A L, Pollak P, Seigneuret E, Hoffmann D, Gay E, Perret J. Chronic VIM thalamic stimulation in Parkinson's disease, essential tremor and extra-pyramidal dyskinesias. Acta Neurochir Suppl (Wien) 1993; 58:39-44.
3. Berkovic S F, Bladin P F. Rubral tremor: clinical features and treatment of three cases. Clin Exp Neurol 1984; 20:119-28.
4. Kim M C, Son B C, Miyagi Y, Kang J K. Vim thalamotomy for Holmes' tremor secondary to midbrain tumour. J Neurol Neurosurg Psychiatry 2002; 73:453-5.
5. Krauss J K, Mohadjer M, Nobbe F, Mundinger F. The treatment of posttraumatic tremor by stereotactic surgery. Symptomatic and functional outcome in a series of 35 patients. J Neurosurg 1994; 80:810-9.
6. Miyagi Y, Shima F, Ishido K, Yasutake T, Kamikaseda K. Tremor induced by toluene misuse successfully treated by a Vim thalamotomy. J Neurol Neurosurg Psychiatry 1999; 66:794-6.
7. Miyagi Y, Shima F, Ishido K, Moriguchi M, Kamikaseda K. Posteroventral pallidotomy for midbrain tremor after a pontine hemorrhage. Case report. J Neurosurg 1999; 91:885-8.
8. Ondo W, Jankovic J, Schwartz K, Almaguer M, Simpson R K. Unilateral thalamic deep brain stimulation for refractory essential tremor and Parkinson's disease tremor. Neurology 1998; 51:1063-9.
9. Pahwa R, Lyons K E, Kempf L, Wilkinson S B, Koller W C. Thalamic stimulation for midbrain tremor after partial hemangioma resection. Mov Disord 2002; 17:404-7.
10. Pezzini A, Zavarise P, Palvarini L, Viale P, Oladeji O, Padovani A. Holmes' tremor following midbrain Toxoplasma abscess: clinical features and treatment of a case. Parkinsonism Relat Disord 2002; 8:177-80.
11. Samadani U, Umemura A, Jaggi J L, Colcher A, Zager E L, Baltuch G H. Thalamic deep brain stimulation for disabling tremor after excision of a midbrain cavernous angioma. Case report. J Neurosurg 2003; 98:888-90.
12. Troster A I, Wilkinson S B, Fields J A, Miyawaki K, Koller W C. Chronic electrical stimulation of the left ventrointermediate (Vim) thalamic nucleus for the treatment of pharmacotherapy-resistant Parkinson's disease: a differential impact on access to semantic and episodic memory? Brain Cogn 1998; 38:125-49.
13. Berk C, Carr J, Sinden M, Martzke J, Honey C R. Thalamic deep brain stimulation for the treatment of tremor due to multiple sclerosis: a prospective study of tremor and quality of life. J Neurosurg 2002; 97:815-20.
14. Critchley G R, Richardson P L. Vim thalamotomy for the relief of the intention tremor of multiple sclerosis. Br J Neurosurg 1998; 12:559-62.
15. Fernandez Gonzalez F, Seijo F, Salvador C, et al. Applied neurophysiology in the deep brain stimulation treatment of multiple sclerosis tremor. Rev Neurol 2001; 32:559-67.
16. Geny C, Nguyen J P, Pollin B, et al. Improvement of severe postural cerebellar tremor in multiple sclerosis by chronic thalamic stimulation. Mov Disord 1996; 11:489-94.
17. Hooper J, Taylor R, Pentland B, Whittle I R. A prospective study of thalamic deep brain stimulation for the treatment of movement disorders in multiple sclerosis. Br J Neurosurg 2002; 16:102-9.
18. Matsumoto J, Morrow D, Kaufman K, et al. Surgical therapy for tremor in multiple sclerosis: an evaluation of outcome measures. Neurology 2001; 57:1876-82.
19. Montgomery E B, Jr., Baker K B, Kinkel R P, Barnett G. Chronic thalamic stimulation for the tremor of multiple sclerosis. Neurology 1999; 53:625-8.

20. Niranjan A, Kondziolka D, Baser S, Heyman R, Lunsford L D. Functional outcomes after gamma knife thalamotomy for essential tremor and MS-related tremor. Neurology 2000; 55:443-6.
21. Whittle I R, Haddow L J. CT guided thalamotomy for movement disorders in multiple sclerosis: problems and paradoxes. Acta Neurochir Suppl (Wien) 1995; 64:13-6.
22. Foote K D, Okun, M S. Ventralis intermedius plus ventralis oralis anterior and posterior deep brain stimulation for posttraumatic Holmes tremor: two leads may be better than one: technical note. Neurosurgery. 2005 April; 56(2 Suppl):E445.
23. Yamamoto T, Katayama Y, Fukaya C, Oshima H, Kasai M, Kobayashi K. New method of deep brain stimulation therapy with two electrodes implanted in parallel and side by side. J Neurosurg 2001; 95:1075-8.
24. Yamamoto T, Katayama Y, Kano T, Kobayashi K, Oshima H, Fukaya C. Deep brain stimulation for the treatment of parkinsonian, essential, and poststroke tremor: a suitable stimulation method and changes in effective stimulation intensity. J Neurosurg 2004; 101:201-9.
25. Deuschl G, Wilms H, Krack P, Wurker M, Heiss W D. Function of the cerebellum in Parkinsonian rest tremor and Holmes' tremor. Ann Neurol 1999; 46:126-8.
26. Lenz F A, Kwan H C, Martin R L, Tasker R R, Dostrovsky J O, Lenz Y E. Single unit analysis of the human ventral thalamic nuclear group. Tremor-related activity in functionally identified cells. Brain 1994; 117 (Pt 3):531-43.
27. Lin Y C, Lenz F A. Effective response evoked by microstimulation of thalamus nuclei in patients with tremor. Chin Med J (Engl) 1993; 106:372-4.
28. Lin Y C, Lenz F A. Distribution and response evoked by microstimulation of thalamus nuclei in patients with dystonia and tremor. Chin Med J (Engl) 1994; 107:265-70.
29. Hirai T, Miyazaki M, Nakajima H, Shibazaki T, Ohye C. The correlation between tremor characteristics and the predicted volume of effective lesions in stereotactic nucleus ventralis intermedius thalamotomy. Brain 1983; 106 (Pt 4):1001-18.
30. Vitek J L, Ashe J, DeLong M R, Alexander G E. Physiologic properties and somatotopic organization of the primate motor thalamus. J Neurophysiol 1994; 71:1498-513.
31. Vitek J L, Ashe J, DeLong M R, Kaneoke Y. Microstimulation of primate motor thalamus: somatotopic organization and differential distribution of evoked motor responses among subnuclei. J Neurophysiol 1996; 75:2486-95.
32. Alexander G E, Crutcher M D, DeLong M R. Basal ganglia-thalamocortical circuits: parallel substrates for motor, oculomotor, "prefrontal" and "limbic" functions. Prog Brain Res 1990; 85:119-46.
33. DeLong M R, Alexander G E, Mitchell S J, Richardson R T. The contribution of basal ganglia to limb control. Prog Brain Res 1986; 64:161-74.
34. Alexander G E, DeLong M R, Strick P L. Parallel organization of functionally segregated circuits linking basal ganglia and cortex. Annu Rev Neurosci 1986; 9:357-81.
35. Delong M R, Georgopoulos A P, Crutcher M D, Mitchell S J, Richardson R T, Alexander G E. Functional organization of the basal ganglia: contributions of single-cell recording studies. Ciba Found Symp 1984; 107:64-82.
36. Wichmann T, DeLong M R. Pathophysiology of Parkinson's disease: the MPTP primate model of the human disorder. Ann N Y Acad Sci 2003; 991:199-213.
37. Wichmann T, DeLong M R. Functional neuroanatomy of the basal ganglia in Parkinson's disease. Adv Neurol 2003; 91:9-18.
38. Bar-Gad I, Bergman H. Stepping out of the box: information processing in the neural networks of the basal ganglia. Curr Opin Neurobiol 2001; 11:689-95.
39. DeLong M R. Functional and pathophysiological models of the basal ganglia: therapeutic implications. Rinsho Shinkeigaku 2000; 40:1184.
40. Wichmann T, DeLong M R. Models of basal ganglia function and pathophysiology of movement disorders. Neurosurg Clin N Am 1998; 9:223-36.
41. Wichmann T, DeLong M R. Functional and pathophysiological models of the basal ganglia. Curr Opin Neurobiol 1996; 6:751-8.
42. Mink J W, Thach W T. Basal ganglia motor control. I. Nonexclusive relation of pallidal discharge to five movement modes. J Neurophysiol 1991; 65:273-300.
43. Lozano A M, Hamani C. The future of deep brain stimulation. J Clin Neurophysiol 2004; 21:68-9.
44. McIntyre C C, Savasta M, Walter B L, Vitek J L. How does deep brain stimulation work? Present understanding and future questions. J Clin Neurophysiol 2004; 21:40-50.
45. Grill W M, Snyder A N, Miocinovic S. Deep brain stimulation creates an informational lesion of the stimulated nucleus. Neuroreport 2004; 15:1137-40.
46. McIntyre C C, Savasta M, Kerkerian-Le Goff L, Vitek J L. Uncovering the mechanism(s) of action of deep brain stimulation: activation, inhibition, or both. Clin Neurophysiol 2004; 115:1239-48.
47. Deuschl G, Bain P. Deep brain stimulation for tremor [correction of trauma]: patient selection and evaluation. Mov Disord 2002; 17 Suppl 3:S102-11.
48. Bornstein R, Cummings G. Parkinson's disease: Neurobehavioral Aspects. New York: Oxford University Press, 1995.
49. Mattis S. Dementia Rating Scale Professional Manual. Odessa, Fla.: Psychological Assessment Resources, Inc., 1973.
50. Mattis S. Dementia Rating Scale: Professional Manual. Odessa, Fla.: Psychological Assessment Resources, 1988.
51. Spitzer R L, Williams J B W, Gibbon M, First M B. The structured clinical interview for DSM-III-R (SCID). I. History, rationale and description. Arch. Gen. Psych. 1992; in press.
52. Stern R A. Assessment of Mood States in Neurodegenerative Disease: Methodological Issues and Diagnostic Recommendations. Semin Clin Neuropsychiatry 1996; 1:315-324.
53. McNair D M, Lorr M, Dropplemar L F. Profiles of Mood States. San Diego: Educational and Industrial Testing Services, 1971.
54. Beck A T. The Beck Depression Inventory. Psychological Corporation. New York, 1978.
55. Beck A T, Beamesderfer A. Assessment of depression: the depression inventory. Psychological Measurements in Psychopharmacology: Modern problems in Pharmacopsychiatry 1974; 7:151-169.
56. Beck J C, Benson D F, Scheibel A B, Spar J E, Rubenstein L Z. Dementia in the elderly: The silent epidemic. Ann Int Med 1982; 97:231-241.
57. Stroop J. Studies of interference in serial verbal reactions. J Exp Psychol 1935; 18:643-662.
58. Petrides M, Milner B. Deficits on subject-ordered tasks after frontal- and temporal-lobe lesions in man. Neuropsychologia 1982; 20:249-62.
59. Gronwall D. Paced auditory serial addition task: A measure of recovery from concussion. Perceptual and Motor Skills 1977; 44:367-373.

60. Lyons K E, Wilkinson S B, Overman J, Pahwa R. Surgical and hardware complications of subthalamic stimulation: a series of 160 procedures. Neurology 2004; 63:612-6.
61. Eskandar E N, Flaherty A, Cosgrove G R, Shinobu L A, Barker F G, $2^{nd}$. Surgery for Parkinson disease in the United States, 1996 to 2000: practice patterns, short-term outcomes, and hospital charges in a nationwide sample. J Neurosurg 2003; 99:863-71.
62. Kondziolka D, Whiting D, Germanwala A, Oh M. Hardware-related complications after placement of thalamic deep brain stimulator systems. Stereotact Funct Neurosurg 2002; 79:228-33.
63. Terao T, Takahashi H, Yokochi F, Taniguchi M, Okiyama R, Hamada I. Hemorrhagic complication of stereotactic surgery in patients with movement disorders. J Neurosurg 2003; 98:1241-6.
64. Fields J A, Troster A I, Woods S P, et al. Neuropsychological and quality of life outcomes 12 months after unilateral thalamic stimulation for essential tremor. J Neurol Neurosurg Psychiatry 2003; 74:305-11.
65. Rehncrona S, Johnels B, Widner H, Tornqvist A L, Hariz M, Sydow O. Long-term efficacy of thalamic deep brain stimulation for tremor: double-blind assessments. Mov Disord 2003; 18:163-70.
66. Beric A, Kelly P J, Rezai A, et al. Complications of deep brain stimulation surgery. Stereotact Funct Neurosurg 2001; 77:73-8.
67. Oh M Y, Abosch A, Kim S H, Lang A E, Lozano A M. Long-term hardware-related complications of deep brain stimulation. Neurosurgery 2002; 50:1268-74; discussion 1274-6.
68. Binder D K, Rau G, Starr P A. Hemorrhagic complications of microelectrode-guided deep brain stimulation. Stereotact Funct Neurosurg 2003; 80:28-31.
69. Lehmann, E L. Nonparametrics: Statistical Methods based on Ranks. Chapter 2, pp. 55-81, Holden-Day, San Francisco, 1975.
70. Lehmann, E L. Nonparametrics: Statistical Methods based on Ranks. Chapter 3, pp. 123-132, Holden-Day, San Francisco, 1975.
71. Vitek J L, Bakay R A, Hashimoto T, Kaneoke Y, Mewes K, Zhang J Y, Rye D, Starr P, Baron M, Turner R, DeLong M R. Microelectrode-guided pallidotomy: technical approach and its application in medically intractable Parkinson's disease. J Neurosurg. 1998 June; 88(6):1027-43.
72. Lozano A M, Hutchison W D. Microelectrode recordings in the pallidum. Mov Disord. 2002; 17 Suppl 3:S150-4.
73. Mandir A S, Rowland L H, Dougherty P M, Lenz F A. Microelectrode recording and stimulation techniques during stereotactic procedures in the thalamus and pallidum. Adv Neurol. 1997; 74:159-65.

What is claimed is:

1. A method of deep brain stimulation (DBS) for treatment of a movement-related disorder associated with the brain, comprising: (a) positioning two or more electrical leads remote with respect to each other in the brain of a subject having need thereof, wherein a first electrical lead is positioned at the ventral intermediate nucleus of thalamus (VIM)/posterior region of nucleus ventralis oralis (VOP) border and a second electrical lead is positioned at the anterior region of nucleus ventralis oralis (VOA)/VOP border; and (b) applying electrical stimulation to at least two of said electrical leads under conditions wherein said electrical stimulation eliminates or ameliorates at least one symptom of the movement-related disorder.

2. The method of claim 1, wherein the movement-related disorder is selected from the group consisting of Parkinson's disease, Huntington's disease, Tourette/OCD, tremor, epilepsy, and dystonia.

3. The method of claim 2, wherein a symptom of the movement-related disorder comprises at least one selected from the group consisting of tremor, rigidity, akinesia, tic, akathesia, restlessness, and gait irregularity.

4. The method of claim 2, wherein the movement-related disorder is a tremor and, wherein the tremor is selected from the group consisting of complex tremor, parkinsonian tremor, dystonic tremor, myoclonic tremor, essential tremor, post-stroke tremor, multiple sclerosis tremor, and post-traumatic tremor.

5. The method of claim 1, wherein stimulation to at least two of said electrical leads eliminates or ameliorates a symptom of the brain disorder to a greater extent than stimulation by one of said electrical leads.

6. The method of claim 1, wherein electrical current is applied intermittently to at least one of the electrical leads.

7. The method of claim 1, wherein electrical current is applied continuously to at least one of the electrical leads.

8. The method of claim 1, wherein electrical current is applied alternately to two or more electrical leads.

9. The method of claim 1, wherein the electrical current is applied concurrently to two or more electrical leads.

* * * * *